United States Patent [19]

Smith et al.

[11] Patent Number: 5,516,700
[45] Date of Patent: May 14, 1996

US005516700A

[54] AUTOMATED URINALYSIS METHOD

[75] Inventors: Jack V. Smith, St. Peter; Jesse M. Carter, Tampa, both of Fla.

[73] Assignee: Chimera Research and Chemical, Inc., Largo, Fla.

[21] Appl. No.: 429,292

[22] Filed: Apr. 24, 1995

Related U.S. Application Data

[63] Continuation of Ser. No. 68,956, May 28, 1993, abandoned.
[51] Int. Cl.$^6$ ................................................. G01D 21/75
[52] U.S. Cl. ........................... 436/164; 436/17; 436/63; 436/175
[58] Field of Search ................ 422/56–58, 61; 436/66, 135, 63, 904, 17–18, 174–176, 164

[56] References Cited

U.S. PATENT DOCUMENTS

| | | | |
|---|---|---|---|
| 3,907,503 | 9/1975 | Betts et al. | 422/67 |
| 4,755,472 | 6/1988 | Ismail et al. | 422/57 |
| 5,128,265 | 2/1992 | Meiattini | 436/17 |

FOREIGN PATENT DOCUMENTS 5256853  3/1992  Japan ....................... 436/17

Primary Examiner—Lyle A. Alexander
Attorney, Agent, or Firm—Herbert W. Larson

[57] ABSTRACT

A method that provides techniques for determination of urinary constituents (Blood (Red Blood Cells/Hemoglobin), Leukocytes, pH, Specific Gravity, Bacterial Reductase/Nitrite/Indole activity, Total Ketone Bodies, Protein, and Glucose) at low chemically significant levels with a carrier independent reagent system that can be placed on a high throughput autoanalyzers. Thus, giving the analyst the ability to run multiple urinary assays on a single sample of urine simultaneously with the ability to compare to reference standards on the same run. This system is designed to neutralize urinary interfering substances. This method is fast, efficient, an adaptable to many of the currently available discrete and continuous flow automated analyzers, effective at sample to reagent ratios of 1 to 13 or more. This method is applicable to samples with high turbidity, high ionic strength, high color content, wide pH extremes, and buffer strengths, among other interfering substances.

4 Claims, No Drawings

AUTOMATED URINALYSIS METHOD

This application is a continuation of Ser. No. 08/068,956 filed May 28, 1993, now abandoned.

BACKGROUND OF THE INVENTION

This invention relates to a method and materials that are designed for use in automating urinalysis. This system is designed to analyze urine for its constituents by a method that is fully automated (does not require the use of manual methods such as refractometer, pH meter, dipsticks, etc). Automation as designed by this system would be directed to the use of a self-operating instrument that is capable of handling multiple reagents designed for use on a automated analyzer system for the quantitative determination of Leukocytes, Blood, pH, specific gravity, Glucose, protein, Bacterial Nitrite, and Total Ketone Bodies in urine.

It is known that the most common method for the analysis of urine is by the use of a manual technique known as a dipstick. This method for the analysis of urine is labor, time intensive, and costly among other detriments. The use of a dipstick for analysis of urine also relies on the subjective interpretation of the technician. The dipstick method requires the technician to submerge the dipstick in a sample of urine and remove it. To wait a specified time, then compare the color development of the test on the dipstick to a color chart. Even more cumbersome methods involve the use of a refractometer, pH meter, or manual chemistry test. The automated urinalysis system offers a method for reducing the consumable materials, and labor costs. The system also offers increased accuracy, sensitivity, and objective quantifiable determinations of urinary constituents for better diagnostic interpretation of the test results of urine, thus enabling a physician to provide better health care for the patient.

In today's atmosphere of rising health care costs and the concomitant reduction in the quality care, a system for the determination of normal or disease state in urine that reduces the cost of testing by decreasing, time, labor, and cost of test materials is called for. An obvious advancement in the science of urinalysis would be to move it from the slow, tedious, and costly techniques such as the dipstick or other manual operations to a fully automateable system that would speed up turn-around-time of obtaining test results, shorten doctor office visits, and reduce overall health care costs. The automated urinalysis system enables a technician to take a sample of urine and place it on an auto analyzer that contains the system reagent materials for each of the above referenced tests, start the self-operating analyzer, and walk away to other duties until the results are reported by the analyzer. Most of the high throughput analyzers currently in use throughout the industry would allow testing in the aforementioned method of hundreds to thousands of urines per hour. This is a marked improvement when compared to manual techniques such as the dipstick which at best would take hours and several technicians to analyze a hundred specimens. An article printed in the American Journal of Clinical Pathology Vol. 83 pages 740–743, discusses the cost of using the dipstick as a screening test for urinalysis. The dipstick methodology can qualitatively determine normal urine constituents. This article states "The urine dipstick procedure costs approximately $0.76 for reagents and 3.0 minutes of the technologist's time". This equates to 20 samples per hour with the use of dipsticks. Another point to make here is that the cost has obviously risen since 1985.

The time is now for the evolution of acceptable techniques for determining normal and abnormal urinary constituents.

The following list of assay devices utilizing prior art includes dry tablets, dipsticks, or other manual techniques for the analysis urinary constituents. None of the prior devices foresee or teach of a multiple/single liquid reagent system designed specifically for auto-analyzers to analyze urinary constituents quantitatively.

One such U.S. Pat. No. 4,147,514 discloses test strips (dipsticks) for the detection of ketone bodies. The assay strips are made up of a chemical bonded to a cellulose pad on a strip. This is then dipped into a specimen sample. This method only determines ketone bodies qualitatively at its best, due to inability of the system to allow the use of standards and controls on the same strip the sample is applied to. This assay does not foresee or teach of a liquid reagent system that is designed to be pumped by an autoanalyzer system into its discrete cuvette and there mixed with a urine sample, and then measured by spectrophotometric means, and followed by a computer driven calculation of a quantitative value derived from standards previously run by the same analyzer. By utilizing an objective instrument (autoanalyzer) which incorporates the use of standards and controls instead of the subjective observation of the naked human eye with no set reference point. The automated urinalysis system can elucidate scientifically verifiable increases in accuracy, precision, and sensitivity yielding quantitative reproducible results. The dipstick method can not accommodate the use of standards, or controls with every sampling of a urine for the calculation and verification of the result, and thus limits its utility to producing a qualitative result only. Nor, does the assay foresee or teach of the specific and unique chemical formulation that the automated urinalysis reagent for ketone bodies is comprised of. Obviously, many advances and differences exist between the automated urinalysis system (herein described) and the prior art. This automated system is a marked advancement in the art of urinalysis.

Another such patent, U.S. Pat. No. 3,146,070 discloses analytical compositions in dry form on a bibulous carrier (dipstick) impregnated with a pH indicator for the determination of pH. This assay at best only determines pH qualitatively, due to the inability to use standards and controls located on the same strip for the same test sample to define and verify a quantitative determination. The assay does not foresee or teach of a liquid reagent system that is designed to be pumped through an auto-analyzer, mixed with urine in a discrete cuvette, measured by spectrophotometric means, and automatically calculate a quantitative value derived from standards run previously on the analyzer. This system also allows for controls to be run periodically to insure continued precision of results. The dipstick method can not accommodate the use of standards or controls with every sampling of a urine for the calculation and verification of result, and thus limits its utility to producing a qualitative result with much less accuracy and precision than the automated urinalysis system. As mentioned and to further illustrate, the dipstick does not have the ability to sample a standard and the unknown solution at the same time, and on the same dipstick, and thus allow determination of a quantitative result. Nor does the assay foresee or teach of the specific and unique chemical formulation that the automated urinalysis reagent for pH is comprised of. Obviously there lies multiple advances and differences that exist between the automated urinalysis system and the prior art. This automated system exhibits a clear, obvious, and marked advancement in the art of urinalysis.

Additionally U.S. Pat. No. 4,318,709 discloses a device comprising a carrier matrix (dipstick) impregnated with the test means for specific gravity. This assay at best only determines specific gravity qualitatively, due to the inability to use standards and controls located on the same strip for the same test specimen. The prior art in this case also did not foresee the wide specimen to specimen matrix variations of real world urine samples including matrix components such as pH, and ionic strength, and the concomitant requirement of a multiple reagent system to effectively analyze urine for specific gravity in a liquid to liquid reaction. The normal pH value for urine can range from 4.5 to 8.0, which if using the prior dipstick method the results would be vastly scattered and inaccurate without a reagent to neutralize the effect prior to completion of the assay. The assay does not foresee or teach of a liquid reagent system that is designed to be pumped through an autoanalyzer, mixed with urine in a discrete cuvette, and measured by spectrophotometric means, and automatically calculate a quantitative value derived from standards previously run on the analyzer. The dipstick method does not have a means for the use of standards or controls with every sampling of a urine for the calculation and verification of a result, and thus limits its utility to producing a qualitative result with less accuracy and precision than the automated urinalysis system. As mentioned and to further illustrate, the dipstick does not have the ability to sample a standard and unknown solution at the same time, and on the same dipstick, and thus allow determination of a quantitative result. Nor, does the assay foresee or teach of the specific and unique chemical formulation that the automated urinalysis reagent for specific gravity is comprised of. Obviously there lies multiple advances and differences that exist between the automated urinalysis system and the prior art. This automated system exhibits a clear, obvious, and marked advancement in the art of urinalysis.

Various devices are described in the literature for the determination of particular urinary constituents one by one with the use of carrier matrices (dipstick, microcapusules, filter paper, etc.). None of the prior art teaches or elucidates a means for determining by automated technology urinary constituents from a single sample of urine, via multiple tests that are reported simultaneously by an autoanalyser using liquid reagents specifically designed for this family of instruments. As cited by the prior art, (in package insert literature) when evaluating laboratory test results, definitive diagnostic, or therapeutic decisions should not be based on any single result or method. However, the prior art states that dipsticks are affected by substances that cause abnormal urine color, such as drugs containing azo dyes (e.g., Pyridium, Azo Gantrisin, Azo Gantanol), nitrofurantoin (Macrodantin, Furadantin), and riboflavin, and thus may affect the readability of reagent areas on the urinalysis reagent strips (dipsticks). The color development on the reagent pad may be masked, or a color reaction may be produced on the pad that could be interpreted visually and/or instrumentally as a false positive or negative. This illustrates the susceptibility of the prior art to erroneous results due to misinterpretation of the color changes (due to subjective observation by analyst), or interference with the reagent color by urinary constituents that yield contradictory color changes, or contamination from adjacent reaction pads spilling interfering color and/or chemicals onto neighboring pads thus causing erroneous results (from cross reaction, inhibition, or activation with test reagents impregnated on test pads). Prior art does not envision or describe the unique formulations needed for such analysis. Furthermore, the prior art does not teach, describe, or elucidate, about a liquid reagent system designed for liquid to liquid reactions without the use of a carrier matrix. Finally, the prior art does not describe, teach, or elucidate, any knowledge of this automated urinalysis system that is capable of the analyzing unknown urine test samples at the same time as standards and controls to allow for the extrapolation of accurate, and reproducible quantitative values, yielding increases in accuracy, precision, and sensitivity. Therefore, it is considered highly desirable to provide a sensitive, rapid, accurate, reliable, time and cost saving, method and device for the determination of urinary constituents. None of the prior art known to the present inventors at the time of filing of the application teaches or suggests the invention presently disclosed and claimed.

OBJECTS AND SUMMARY OF THE INVENTION

In retrospect this invention is the answer to many of the problems unanswered by the prior art: quantitative results, non-subjective results, reproducible results, increased accuracy, precision, sensitivity, carrier free reagents, reagents designed for autoanalyzer use, reagents uniquely designed for each particular urine analyte assay overcoming matrix problems previously unanswered by prior art, a method allowing vast improvement of test completion time (hundreds to thousands per hour). The present invention presents a fully automateable walk-away urinalysis system applicable to any discrete autoanalyzer currently in use, and obviously represents a marked advancement in art of urinalysis. The clear cut object of the present invention is to provide a more comprehensive method for determining urinary constituents (Leukocytes, Blood, Bacterial Nitrite/Indole/reductase activity, Total Ketone Bodies, Glucose, Protein, pH, and specific gravity) that in general benefit society as a whole and specifically yield improved health care.

Thus, it is a primary objective of the present invention to provide techniques for determination of urinary constituents (Blood (Red Blood Cells/Hemoglobin), Leukocytes, pH, Specific Gravity, Bacterial Reductase/Indole/Nitrite activity, Total Ketone Bodies, Protein, and Glucose) at low chemically significant levels. These methods must be fast, efficient, adaptable to many of the currently available discrete and continuous flow automated analyzers, effective at sample to reagent ratios of 1 to 13 or more (unlike like the prior art, because this ability is essential for application to most autoanalyzers), and applicable to samples with high turbidity, high ionic strength, high color content, and wide pH extremes, and buffer strengths among other interfering substances.

An additional object of this invention is to make available an advanced method for analyzing a sample of urine for the quantitation of its constituents on an autoanalyzer. The advanced ability of the automated urinalysis system to offer a means for automated analysis on urine is a significant improvement the in art of urinalysis.

Additionally, the object of this invention is to provide a comprehensive method which is broadly adaptable to a wide variety of automated analyzers presently in use in the industry which will increase accuracy, sensitivity, precision, and speed. An autoanalyzer would also allow for precise quantitative results which are beyond the scope and abilities of the prior art. An autoanalyzer used in conjunction with the present invention automated urinalysis reagents would also provide a system that can produce an objective quantitative result of an unknown urine sample obtained from a linear standard curve determined by analysis of standards run on the instrument, and verified as accurate by quantifying controls of known value. This simultaneous analysis of standards and unknowns (urine samples) yielding unbiased results would improve the art of urinalysis significantly over the prior art, which yields only qualitative and subjective results.

It is a further object of this invention to provide a method for the simultaneous determination of multiple urinary components (Leukocytes, Blood, Bacterial Reductase/Nitrite/Indole activity, Total Ketone Bodies, pH, Specific Gravity, Protein) from a single urine sample using a system of reagents designed for autoanalyzer use. This improvement in the science of urinalysis over the prior art will prove to be significant medically and economically.

Another object of this invention is to provide a method that yields quantifiable results in the determination of urinary constituents present in a sample of urine. None of the prior art teaches, elucidates, or envisions a method for the determination of quantitative values for urinary constituents: Leukocytes, Blood, Bacterial reductase,/Nitrite/Indole activity, Total Ketone Bodies, pH, specific gravity, Glucose, Protein. The prior art can provide only qualitative results. For example, using current art a technician must dip a urine stick into a sample, remove, observe and record color changes for eight separate test blocks on the strip. Each of these eight tests require accurate, precise, and specific and different times for color development, and the technologist must measure them accurately while judging and recording the relative intensities of various shades of color. This obviously cumbersome, time intensive, subjective, inaccurate, method can vastly be improved upon by the use of the present invention.

Still another object of this invention is to provide a method for the determination of objective results (from the photometric analysis by the automated analyzer) instead of the subjective determination (from human observation). The present invention provides a unique formulated reagent system that can be mixed with unknown urine samples, standards, and controls and then be read spectrophotometrically with unbiased accuracy on an autoanalyzer. The use of the automated urinalysis system provides a means for improved accuracy, precision, and specificity by removal for the subjective human element from the analysis. Clearly, a system that automatically dispenses, measures, and records results is a marked improvement in the science of urinalysis.

Yet another object of this invention is to provide uniquely formulated reagents for each urinalysis assay that were not taught or envisioned by the prior art, and overcome the inadequacies of the prior art. The analysis for Blood in urine in the prior art is a carrier dependent assay that is susceptible to interference urea, vitamin C, and high levels of some other normal urinary constituents. Consider the fact that urea is the largest component of urine (besides water) by a factor of 50% over the next largest component (sodium chloride). A unique chemical formulation to compensate for urea would be an advancement in the art of urinalysis. The present invention is a liquid reagent that is not carrier dependent, designed for autoanalysis, and has agents added to remove the urea and other interfering ions from the solution, thus preventing it from interacting with the color developer. These improvements increase sensitivity, accuracy, and precision, thereby allowing the Blood assay in urine to be quantifiable.

Yet another object of this invention is to provide uniquely formulated reagents for each automated urinalysis assay that was not taught or envisioned by the prior art, and overcomes the inadequacies of the prior art. The assay for pH in the prior art is limited to a carrier dependent assay (i.e., solid matrix), and its sensitivity is limited to qualitative whole number units. It has a non-specific s-shaped curve with 7 color changes for determination of pH within the very small range of pH 5 to pH 8.0. These different color changes make analysis by an autoanalyzer's single wavelength (monochromatic) spectrometry impossible. Another problem with this assay is the inaccuracy introduced by the subjective interpretation of changes in color gradations and shades by the technician and the inability of color-blind people to perform the test. The prior art is a matrix dependent method that cannot be used in a carrier free liquid reagent system designed for autoanalysis. The multitude of color changes including orange, yellow, blue, green, and intermediates shades make the use of the prior art impossible for quantitative, sensitive, accurate, and precise monochromatic spectrophotometric analysis. The present invention is a liquid reagent that is not carrier dependent, and is designed for use on autoanalyzers. The present invention is linear from pH of 3.0 to a pH of greater than 10.0. The present invention has a curve stabilizer added to increase curve stability and to provide a flat line analysis, thus removing the s-shaped curve phenomena. The present invention is quantifiable to within 0.01 pH units. It is more precise, accurate, and sensitive than the prior art, and thus represents an obvious advancement in the art of urinalysis.

Yet another object of this invention is to provide uniquely formulated reagents for each automated urinalysis assay that was not taught or envisioned by the prior art. The assay for Leukocytes in the prior art has limited accuracy and application because it is carrier dependent, it only produces qualitative results (i.e., trace, 1+, 2++, 3+++, or a range 5 to 15 leukocytes present), it yields numerous color changes (5) making objective monochromatic spectrophotometric analysis impossible, and it cannot be easily and effectively converted to a liquid matrix, which is required for widespread autoanalyzer use. The prior art is susceptible to interference from sample urine matrices including but not limited to high ionic strength, antibiotics, and glucose. The prior also takes a minimum of 2 minutes for color development and subjective interpretation of results. The present invention is a liquid reagent that is not carrier dependent, and is specifically designed for use on autoanalyzers. The present invention is quantitatively linear from 0.0 esterase units of activity to greater than a 100 esterase units of activity (0 to 25 Leukocytes and greater). The present invention directly measures the amount of leukocytes present by quantitatively measuring the leukocyte esterase activity in urine. This is accomplished by a colormetric reagent specifically designed for use on an autoanalyzer, and is sensitive to leukocyte esterase. The present invention includes a compensator (buffer) for adjusting the pH of the urine samples because random samplings can range from 4.5 to 8.0. Buffering the sample is critical to obtaining optimal sensitivity, and precision because Leukocyte esterase activity is optimal at a pH of 6.8. Due to its solid matrix the prior art is incapable of compensating for abnormal pH resulting in its poor sensitivity and precision. The present invention has curve stabilizers and agents added to compensate for the wide variety of interfering substances found in urine, which the prior art does not teach or envision. The present invention is quantitative, carrier independent, precise, accurate, and sensitive, and would be an advancement in the art of urinalysis.

Yet another object of this invention is to provide uniquely formulated reagents for each automated urinalysis assay that was not taught or envisioned by the prior art. The assay for Bacterial reductase/Nitrite/Indole activity, in the prior art has limited application and accuracy because it is carrier dependent, and it only produces qualitative results (i.e., positive or negative with a range of 0.06 to 0.1 mg/dl of nitrite ions present). The measurement of nitrite is a indirect method suggesting the presence of gram negative micro organisms that reduce nitrate to nitrite. Urinary tract infections can occur from organisms that do not convert nitrate to nitrite (i.e., gram positive), thus a false negative would occur. If dietary nitrate were absent, the gram negative bacteria could not make nitrite again resulting in a false negative test. If the urine is not held in the bladder for at least 4 hours a false negative can again result, because the bacteria require this time to convert nitrate to nitrite in sufficient quantities for detection. It should be noted that frequent urination is often associated with bacterial urinary infection. The prior method yields a non-specific color development for determination of Nitrite present making objective and monochromatic spectrophotometric analysis difficult. Extrapolation of prior to the present invention is not readily apparent to anyone schooled in the art of urinalysis. The prior art is susceptible to interferences from sample matrices including, but not limited to high ionic strength and Vitamin C. The present invention is a liquid reagent that is not carrier dependent, and is specifically designed for use on autoanalyzers. The present invention is quantitatively linear from 0.05 mg/dl to 1.0 mg/dl nitrite ions present. The present invention also directly measures quantitatively the amount of reductase present (which is the enzyme present that converts nitrate to nitrite). There are several advantages to measuring the reductase including, but not limited to more direct measurement of bacteria present, bladder incubation time not required, and resulting assay is more accurate, sensitive, and quantitative. The present invention utilizes colormetric reagents specifically designed for autoanalyzer, and can directly measure the amount of nitrite ion, indole activity, or reductase present. The present invention has a compensator for the pH of the random urine sample which can range from 4.5 to 8.0. It should be noted that Nitrate reductase activity is optimal at a pH of 6.8. Buffering the sample to this pH is critical to obtaining optimal sensitivity, accuracy, and precision. The present invention measures the activity of nitrate reductase on nitrate (substrate) by the disappearance of NADPH which absorbance can be monitored at 340 nm. The prior art has no means to compensate for abnormal pH, resulting in poor sensitivity and selectivity of the assay. The present invention has curve stabilizers and agents to compensate for a variety of interfering substances found in urine, which the prior art did not teach or envision. The present invention is quantitative, carrier independent, precise, accurate, automateable, and sensitive, and represents an obvious advancement in the art of urinalysis.

Another object of this invention is to provide uniquely formulated reagents for each automated urinalysis assay that was not taught or envisioned by the prior art. The assay for specific gravity in the prior art has limited accuracy and application because it is a carrier dependent assay, and it only produces semi-qualitative results ranging from 1.000 to 1.030 specific gravity units in increments of 5 specific gravity units (i.e., 1.000, 1.00, 1.010, 1.015, 1.020 . . . ). The prior art can not extrapolate a more sensitive quantitative value (i.e., 1.003, 1.004, . . . ). The prior method produces a multitude of changes in color gradations and shades (at least 7 different color changes) making accurate, precise, objective, monochromatic spectrophotometric autoanalysis impossible. Someone skilled in the prior art could not convert it to a liquid matrix as required for use on autoanalyzers. The prior art is susceptible to interferences from sample matrices including, but not limited to high or low pH, elevated urinary protein, and highly buffered urines. The prior art also requires 45 seconds incubation period for test completion increasing the chance of operator error and cost of testing. The present invention is a liquid reagent that is not carrier dependent, and is specifically designed for use on autoanalyzers. The present invention is quantitatively linear from 1.000 to 1.050 with precision of plus or minus 0.0005 specific gravity units. The present invention is a colormetric reagent system specifically designed for autoanalyzer use that is sensitive to ions in solution. The present invention has a compensator for highly buffered urines, and diverse urinary pH which can range from 4.5 to 8.0 in random urines. The prior art did not teach or elucidate a method to neutralize the pH and buffer activity of a urine prior to assaying for ion content. This failure of the prior art to compensate for abnormal pH directly contributes to its poor accuracy and precision. The present invention has curve stabilizers and agents added to compensate for the wide variety of interfering substances found in urine, which the prior art did not teach or envision. The present invention is quantitative, carrier independent, precise, accurate, and sensitive, and is an obvious advancement in the art of urinalysis.

Again, another object of this invention is to provide uniquely formulated reagents for each automated urinalysis assay that was not taught or envisioned by the prior art. The assay for Total Ketone Bodies in the prior art has limited accuracy and application because it is a carrier dependent assay and it only produces semi-qualitative results ranging from 5 to 10 mg/dl acetoacetic acid. The prior method produces a multitude of changes in color gradations and shades (at least 6 different colors) for determination of ketone bodies making accurate, precise, and monochromatic spectrophotometric autoanalysis impossible. Some one skilled in the prior art could not easily and effectively convert it to a liquid matrix, as required for use on an autoanalyzer. The prior art is qualitative and only measures acetoacetic acid which constitutes only 20% of the total ketone bodies present in urine. Please note that B-Hydroxybutyric acid makes up approximately 80% of the ketone bodies present in urine. The prior art is susceptible to interferences from sample matrices including, but not limited to highly pigmented urines, sulfhydryl groups (causing false positive results), high or low pH values, levodopa metabolites, mesna (2-mercaptoethane sulfonic acid) causing false positive results, atypical color development and high ionic strength urines. The prior art also requires 40 seconds incubation period for test completion increasing the chance of operator error, and cost of testing. The present invention is a liquid reagent that is not carrier dependent, and is specifically designed for use on autoanalyzers. The present invention is quantitatively linear from 0.0 to 25 mg/dl of acetoacetic acid or greater in increments of 0.1 mg/dl. The present invention also measures quantitatively the amount of B-hydroxybutyric acid present with a sensitivity range of 0.0 mg/dl to 100 mg/dl B-hydroxybutyric acid. This is done by the use of a colormetric reagents specifically designed for autoanalyzer use that are sensitive to the presence of acetoacetic acid and B-Hydroxybutyric acid in solution. The present invention has a compensator for highly buffered urines, and diverse urinary pH which can range from a pH of 4.5 to 8.0 in random urines. The prior art did not teach of or elucidate a method to neutralize the pH and ionic content of a urine prior to assaying acetoacetic acid content. This failure of the prior art to compensate for abnormal pH and buffering directly contributes to its poor accuracy and precision. This lack of precision and accuracy of the prior art is also directly attributable to its lack of sensitivity to B-Hydroxybutyric acid, the major component of ketone bodies present in urine. The present invention has curve stabilizers and agents added to compensate for the wide variety of interfering substances found in urine, which the prior art did not teach or envision. The present invention measures the presence of B-hydroxybutyric acid in urine at the same time or separately with acetoacetic acid quantitation, thus greatly enhancing its accuracy and precision. The present invention is quantitative, carrier independent, precise, accurate, and sensitive, and represents an obvious advancement in the art of urinalysis.

Yet another object of this invention is to provide uniquely formulated reagents for each automated urinalysis assay that were not taught or envisioned by the prior art. The assay for Protein in the prior art is limited to a carrier dependent assay that is only semi-qualitative producing results ranging from 15 to 30 mg/dl protein. The prior method yields non-specific color development with more than 6 different colors changes for determination of protein making objective and monochromatic spectrophotometric analysis impossible. Someone skilled in the art cannot easily elucidate or convert the prior art into the matrix required for use on autoanalyzers. The prior art only semi-qualitatively measures protein in the form of albumin which constitutes only 30% of the urinary protein excreted in urine. Please note that the majority of protein excreted in urine is in the form of globulins. The prior art is also susceptible to interference due to, but not limited to highly buffered urine, urine with high pH values, quaternary ammonium compounds (i.e., from some antiseptics and detergents) or skin cleaners containing chlorhexidine, and other normal urinary constituents. The reagent and high ionic strength urine. The prior art also requires a carefully measured 60 second period to obtain correct analytical results. The present invention is a liquid reagent that is not carrier dependent, and is specifically designed for use on most currently available autoanalyzers. The present invention is quantitatively linear from 0.0 to 100 mg/dl of protein with precision of 0.1 mg/dl. The present invention quantitatively measures the amount of globulin accounting for approximately 70% in urine, and albumin (approximately 30%) accurately in the range of 0.0 mg/dl to 100 mg/dl. This is done by the use of a colorimetric reagents specifically designed for autoanalyzer use and are sensitive to protein in the form of albumin and globulins. The present invention has a compensator for pH (which can range from a pH of 4.5 to 8.0), and highly buffered urines. The prior art did not teach of or elucidate a method that would neutralize the pH and ionic strength of a urine prior to analysis of protein content. The prior art has no means to compensate for abnormal pH, contributing to its poor sensitivity and selectivity to the presence of protein in the urinary sample matrix. The present invention has curve stabilizers and agents added to compensate for the wide variety of interfering substances found in urine. These innovations were not taught or envisioned by the prior art. The present invention measures the quantity of albumin and globulin in urine simultaneously, or separately. The present invention is quantifiable, carrier independent, precise, accurate, and sensitive method, and represents an obvious advancement in the art of urinalysis.

Yet another object of this invention is to provide uniquely formulated reagents for each automated urinalysis assay that was not taught or envisioned by the prior art. The assay for Glucose in the prior art is limited to a carrier dependent assay that produces only qualitative results ranging from 75 to 125 mg/dl of glucose. The prior method yields color development with more than 6 different color changes for the determination of glucose making subjective, monochromatic, and spectrophotometric analysis impossible. Furthermore, someone skilled in the art cannot easily elucidate or converts the prior art into the liquid matrix required for use on autoanalyzers. The prior art only qualitatively measures glucose. The prior art is also susceptible to interference from, but is not limited to high ionic strength urines, Vitamin C, and Ketone Bodies. The prior art also requires a carefully measured 30 second incubation period to obtain correct semi-qualitative results. The present invention is a liquid reagent that is not carrier dependent, and is specifically designed for use on autoanalyzers. The present invention is quantitatively linear from 0.0 to 250 mg/dl glucose with precision to 0.1 mg/dl. The present invention also quantitatively measures the amount of glucose. This is done by the use of a colormetric reagents that are sensitive to the presence of urinary glucose, and are specifically designed for use on autoanalyzers. The present invention has a compensator for the pH (which can range from a pH of 4.5 to 8.0 in random urines). The prior art did not teach, or elucidate a method that would neutralize the pH and ionic strength of a urine prior to analysis of glucose content. The prior art has no means to compensate for abnormal specific gravity, which contributes to its poor sensitivity and selectivity to the presence of glucose in the urinary sample matrix. The present invention has curve stabilizers and agents added to compensate for the wide variety of interfering substances found in urine, which the prior art did not teach or envision. The present invention is quantitative, carrier independent, precise, accurate, and sensitive, and represents an obvious advancement in the art of urinalysis.

Other objects and a fuller understanding of the invention will be had by referring to the following description and claims of the preferred embodiment and will become apparent to those skilled in the art.

DETAILED DESCRIPTION OF THE INVENTION

The presently claimed method comprises a group of carrier-free liquid reagents designed for simultaneous usage on automated analyzers for quantitative determination of urinary constituents. The automated urinalysis system of the instant invention solves the problems confronting automating the analysis of urine, and in the process represents a significant improvement over the present art. These improvements which permit (facilitate) application to automation and represent significant technical improvement over the previous art include, a buffering system for pH variation in urine by correcting pH to the analytically preferred value prior to analysis, and also stabilizing reaction rates thereby improving linearity and neutralizing the interference effects of the highly complex matrix of random urines submitted for analysis. Additional technical improvement is due to the addition of components to remove interfering substances yielding reduced assay limitations and increased linearity, accuracy, and precision in the resulting quantitations. These unique reagent formulations allow automation resulting in (but not limited to) enhanced, speed, objectivity, accuracy, and sensitivity associated with a synopsis of the automated testing process follows. The entire automated urinalysis reagent system is then loaded into an autoanalyzer, the controls, standards, and unknown urine samples are fed into the autoanalyzer, individually mixed with each test reagent in discrete cuvettes, the absorbance read, and quantitation determined for comparison with the standard curve.

The composition of each reagent of the present invention is designed for optimum reaction with the random urine samples and to effectively deal with problems arising from the tremendous variability from sample to sample due to the diet, disease state, medications, time of collection, state of hydration, sex, age, and physical well being of the patient. All of the factors can interfere with the previous art.

The automated urinalysis system reagents are individually designed for optimum analysis of the specific urinary component. The reagent system to detect Blood (RBC's)in urine is carrier-independent, and contains specific agents added to compensate for interference by urea, vitamin C, high ionic levels (specific gravity), abnormal pH, and other normal urinary constituents. The RBC reagent system is composed of two reagents (but can be consolidated into one). The first reagent (R1) is specifically designed to neutralize matrix interference and increase sample-reagent compatibility, with the autoanalyzer. 2,3-Butanedione monoxime is added to the first reagent (R1) to remove urea, and other substances in the urine sample that cause interference with colormetric reactions utilizing any of the following components 3,3',5,5'-Tetramethylbenzidine, Dicarboxidine, 3- Methyl-2- benzothiazolinone hydrazone, or N,N- dimethylaniline. The components listed above are particularly susceptible to interference from urea (a major component of urine). Ethylenediaminetetraacetic acid (disodium salt) and dimercaptopropanol are other components of the R1 used to neutralize interfering substances by chelation, and anti-oxidant activity. This compound removes oxidizing contaminants such as hypochlorite, and acts as a solution clarifyer (it causes the disappearance of the characteristic yellow color of urine), thereby enhancing spectrophotometric analysis. 2,3-Diphosphoglycerate is added to affect the oxygen dissociation of hemoglobin. Saponin is present to lyse the red blood cells that may be present and intact in urine, thus releasing the hemoglobin contained within. Note that 2,3-Diphosphoglycerate in the alkaline reagent mixture causes the dissociation constant of hemoglobin to shift to the left (acid Bohr effect), thus increasing the affinity of hemoglobin for oxygen and forcing the reaction to completion. Oxygen is provided by the reaction of hemoglobin with hydrogen peroxide. Sodium azide is added to stabilize hydrogen peroxide. The R1 contains hydrogen peroxide acting as a substrate for the peroxidase activity of the heme fraction of hemoglobin which is a major component of red blood cells. The R1 also contains a buffer to adjust sample pH and aid in solubility and compatibility R1's complex chemical matrix. This complex reagent matrix requires a complementary buffering system with unique dynamics, capable of adjusting the reaction solution to the ideal pKa, and promoting component solution compatibility in an aqueous medium autoanalyzers. Unbuffered solutions may have high acidic or basic activity, or strictly organic properties which are not compatible with autoanalyzer syringes, tubing, metal, and plastic parts. This reagent system buffer is designed to correct these problems. The buffers also promote carrier independence. The R1 also contains surfactants that decrease surface tension, promote effective mixing on a molecular level, and improve flow dynamics through tubing and syringes of automated analyzers. The concentrations of R1 buffers and components can be varied to compensate for limitations and variations in the configuration of sampling and reagent delivery systems of various makes of autoanalyzers. The R1 components compensate for abnormal urinary pH, and highly buffered urines. Ampyrone is added to the R1 to promote, or catalyze the reaction of the afore mentioned oxidized peroxide molecule with a coupling agent such as p-hydroxybenzoic, N-Ethyl-N-sulfohydroxypropyl-m-toluidine (TOOS), 2-Hydroxy-3,5-dichlorobenzenesulfonate sodium salt (HDCBS), 2,2'-Azino-di- 3-ethylbenzthiazoline sulfonic acid diammonium salt (ABTS), or trinder, or phenolic substitutes. The addition of Pyrogallol is added to R1 and acts as a substrate that is oxidized by the oxygen radical released when the heme (peroxidase active) molecule reacts with hydrogen peroxide in solution.

The second reagent (R2) of the 2 part reagent system for Blood (if a single reagent system for Blood is not used) is composed of one, or more of the following: 3,3',5,5'-tetramethylbenzidine, dicarboxidine, pyrogallol, hydrogen peroxide, 3-methyl-2-benzothiazone hydrazone, N,N-dimethylaniline, benzidine, o-dianisidine, and oxidized phenothiazines in solution. This reagent is buffered according to which group or single component is used. This buffer contained in R2 adjusts sample pH and aids in solubility and compatibility of R2's complex chemical matrix. This complex reagent matrix requires a complementary buffering system with unique dynamics capable of adjusting the reaction solution to the ideal pKa's, establishing carrier independence, and promoting component solution compatibility in an aqueous medium with autoanalyzers. Unbuffered solutions may have high acidic or basic activity, or strictly organic solubilities properties which are not compatible with autoanalyzer syringes, tubing, metal, and plastic parts. The R2 also contains surfactants that decrease surface tension, promote effective mixing on a molecular level, enhance carrier independence, and improve flow dynamics through tubing and syringes of automated analyzers. The combinations and concentrations of R1 and or the R2 components can be varied due to limitations and variations in the configuration of sampling and reagent delivery systems of different makes of autoanalyzers. Without further elaboration, it is believed that one skilled in the art can, using the preceding description, effectively utilize the present invention. The following preferred specific embodiments are, therefore, to be merely illustrative, and not limitive of the remainder of the disclosure of the present invention in any way whatsoever. In the following examples, all instrument parameters, reagent combinations, and method techniques are generalized.

EXAMPLE 1

The automated RBC urinalysis reagent system's first reagent (R1) contains surfactant, 2,3-Butanedione monoxime, ethylenediametetraacetic acid, dimercaptopropanol, saponin, 2,3- Diphosphoglycerate, and buffer. The second reagent (R2) consists of surfactant, buffer, 3,3',5,5'-tetramethylbenzidine in 10% lactic acid. These reagents are placed in the autoanalyzer. The urine samples, standards, and controls are placed in the autoanalyzer specimen cups. The urine samples, standards, and controls, are aliquoted into cuvettes, mixed with the first reagent,and than mixed with the second reagent, and then read at specified intervals as dictated by the instrument parameters, and at the specified wavelengths (monochromatically) depending on reagent combination used. In this instance the assay should be read at 660 nanometers with read times specific to the analyzer.

EXAMPLE 2

The automated RBC urinalysis single reagent system would contain (all or some of the following:) 2,3-Butanedione monoxime, ethylenediametetraacetic acid, dimercaptopropanol, 2,3-Diphosphoglycerate, Ampyrone, Sodium azide, hydrogen, peroxide, saponin, p-Hydroxybenzoic acid, N-Ethyl-N-sulfohydroxypropyl-m-toluidine, surfactants, The reagents are placed on the autoanalyzer. The urine samples, standards, and controls are placed in the autoanalyzer specimen cups. The urine samples, standards, and controls, are aliquoted into cuvettes, mixed with the reagent, and the solutions are read at specified intervals as dictated by the instrument parameters and the specified wavelength (monochromatically) depending on the reagent combination used. In this instance, the assay should be read at 505 nanometers read times are specific to the analyzer.

EXAMPLE 3

In the automated RBC urinalysis reagent system, first reagent (R1), contains surfactants, buffer, 2,3- Butanedione monoxime, dimercaptopropanol, saponin, 2,3- Diphosphoglucerate, and ethylenediametetraacetic acid. The second reagent (R2) consists of, hydrogen peroxide, Sodium azide, 3-methyl-2-benzothiazoline hydrazone, N,N-dimethylanilane, buffers, and surfactants. The reagents are placed on the autoanalyzer. The urine samples, standards, and controls are placed in the autoanalyzer specimen cups. The urine samples, standards, and controls, are aliquoted into cuvettes, with the first reagent, the second reagent is then added and mixed, and the solutions are then read at specified intervals as dictated by the instrument parameters at the specified wavelength (monochromatically) depending on the reagent combination used. In this instance the assay should be read at 585 nanometers and read times are specific to the analyzer.

EXAMPLE 4

In the automated RBC urinalysis reagent system's first reagent (R1) contains surfactant, 2,3-Butanedione monoxime, ethylenediametetraacetic acid, dimercaptopropanol, saponin, 2,3-Diphosphoglycerate, and buffer. The second reagent R2 consist of surfactant, buffer, o-dianisidine. The reagents are placed on the autoanalyzer. The urine sample, standards, and controls are placed in the autoanalyzer specimen cups. The urine samples, standards, and controls are aliquoted into cuvettes, mixed with the first reagent, the second reagent is then added and mixed, and the solutions are then read at specified intervals as dictated by the instrument parameters at the specified wavelength (monochromatically) depending on the reagent combination used. In this instance the assay should be read at 540 nanometers and read times are specific to the analyzer.

EXAMPLE 5

In the automated RBC urinalysis single reagent system would contain (all or some of the following:), 2,3-Butanedione monoxime, Pyrogallol, ethylenediametetraacetic acid, dimercaptopropanol, p-hydroxybenzoic acid, saponin, 2,3-Diphosphoglycerate, Sodium azide, hydrogen peroxide, N-ethyl-N-(2-hydroxy-3-sulfopropyl)-m-toluidine, surfactants, are added. The reagents are placed on the autoanalyzer. The urine samples, standards, and controls are placed in the autoanalyzer specimen cups. The urine samples, standards, and control, are aliquoted into cuvettes, mixed with the reagent, and the solutions are read at specified intervals as dictated by the instrument parameters at the specified wavelength (monochromatically) depending on reagent combination used. In this instance, the assay should be read at 550 and read time is specific to the analyzer.

EXAMPLE 6

In the automated RBC urinalysis reagent system's first reagent (R1) contains surfactant, 2,3-Butanedione monoxime, ethylenediametetraacetic acid, dimercaptopropanol, saponin, 2,3-Diphosphoglycerate, and buffer. The second reagent R2 consist of surfactant, buffer, oxidized phenothiazines. The reagents are placed on the autoanalyzer. The urine samples, standards, and controls are placed in the autoanalyzer specimen cups. The urine samples, standards, and controls are aliquoted into cuvettes, mixed with the first reagent, then the second reagent is then added and mixed, and the solutions are then read at specified intervals as dictated by the instrument parameters at the specified wavelength (monochromatically) depending on the reagent combination used. In this instance the assay should be read at 540 nanometers and read times are specific to the analyzer.

EXAMPLE 7

In the automated RBC urinalysis reagent system's first reagent (R1) contains surfactant, 2,3-Butanedione monoxime, ethylenediametetraacetic acid, dimercaptopropanol, saponin, 2,3-Diphosphoglycerate, hydrogen peroxide, sodium azide, and buffer. The second reagent R2 consist of surfactant, buffer, Ampyrone, p-Hydroxybenzoic acid, and phenol. The reagents are placed on the autoanalyzer. The urine samples, standards, and controls are placed in the autoanalyzer specimen cups. The urine samples, standards, and control are aliquoted into cuvettes, mixed with the first reagent, the second reagent is then added and mixed, and the solutions are then read at specified intervals as dictated by the instrument parameters at the specified wavelength (monochromatically) depending on the reagent combination used. In this instance the assay should be read at 505 nanometers and read times are specific to the analyzer.

EXAMPLE 8

In the automated RBC urinalysis reagent system's first reagent (R1) contains 2,3-Butanedione monoxime, ethylenediametetraacetic acid, dimercaptopropanol, 2,3-Diphosphoglycerate, Sodium azide, hydrogen peroxide, saponin, surfactants,and buffers. The second reagent (R2) has buffers, surfactants, N-Ethyl-N-sulfohydroxypropyl-m-toluidine. The reagents are placed on the autoanalyzer. The urine samples, standards, and controls are placed in the autoanalyzer specimen cups. The urine samples, standards, and control, are aliquoted into cuvettes, mixed with the first reagent, the second reagent is then added and mixed, and the solutions are then read at specified intervals as dictated by the instrument parameters at the specified wavelength (monochromatically) depending on the reagent combination used. In this instance the assay should be read at 550 nanometers and read times are specific to the analyzer.

EXAMPLE 9

In the automated RBC urinalysis reagent system's first reagent (R1) contains 2,3-Butanedione monoxime, ethylenediametetraacetic acid, dimercaptopropanol, 2,3-Diphosphoglycerate, Sodium azide, hydrogen peroxide, saponin, surfactants, buffers. The second reagent (R2) consists of buffers, surfactants, N-Ethyl-N-sulfohydroxypropyl-m-toluidine (TOOS), and/or (one or more from the following group: 2,2'Azino-di-(3-ethylbenzthiazoline sulfonic diammonium salt (ABTS), 2-Hydroxy-3,5-dichlorobenzenesulfonate sodium salt (HDCBS), or other suitable trinder reagent). The reagents are placed on the autoanalyzer. The urine samples, standards, and controls are placed in the autoanalyzer specimen cups. The urine samples, standards, and controls are aliquoted into cuvettes mixed with the first reagent, the second reagent is then added and mixed, and the solutions are then read at specified intervals as dictated by the instrument parameters at the specified wavelength (monochromatically) depending on the reagent combination used. In this instance the assay should be read at 550 nanometers secondary wavelength and read times are specific to the analyzer.

The automated urinalysis system reagents are individually designed for optimum analysis of specific urinary components. The reagent system for Leukocytes (WBC) in urine is carrier-independent, and has specific agents added to compensate for interference caused by enzyme inhibitors, oxalic acid, high ionic strength urines (specific gravity), glucose, antibiotics (Tetracycline), cephalexin, cephalothin, abnormal pH values, and other normal urinary constituents. The reagent system is composed of a single reagent (but can be a two reagent system). This reagent system is specifically designed for matrix interference neutralization, and automated liquid reagent compatibility. The component 2,3-Butanedione monoxime is included in this reagent to remove urea, and other substances found in urine that cause interference with the colormetric reactions. Examples: of interference include free radical oxidation of 3-indoyl acetate, p-nitrophenyl stearate, phenyl laurate, N-toluene sulfonyl alanine indole ester, derivatized pyrrole amino acid ester, or other active esters in random urine specimens due to many components found in Ethylenediaminetetraacetic acid (disodium salt) and dimercaptopropanol are components added to the reagent and used to neutralize interfering substances by chelating, remove enzyme inhibitors, and anti-oxidant activity. This removes oxidizing contaminants such as hypochlorite and heavy metals which are enzyme inhibitors, and act as a solution clarifyer (it causes the disappearance of the characteristic yellow color of urine) thereby enhancing spectrophotometric analysis. These interference neutralizing compounds can be added to the reagent to react competitively with the interfering substances, and enhance Leukocyte esterase activity. The reagent may also contain bile salts, albumin and calcium ions (calcium chloride) to increase esterase activity. Other enzyme activators are added such as Calcium chloride (or other as magnesium chloride etc.). These agents act to inhance activity of the esterase as well as prevent denaturation of the enzyme. The reagent may also contain hydrogen peroxide as a substrate (oxygen donor) for peroxidase. Peroxidase and hydrogen peroxide intreact to yeild an oxygen radical. This radical acts to enhance the color developing properties (speed, completeness, of reaction, ect.) of the reagent system. Sodium azide is present as a hydrogen peroxide stabilizer. The reagent also contains a buffer to adjust sample pH and aid in solubility, and compatibility of the reagents complex chemical matrix. This complex chemical matrix requires a complementary, aqueous buffering system with unique dynamics capable of adjusting the reaction solution to the ideal pKa, and promoting reagent component compatibility with autoanalyzers. Unbuffered solutions may have high acidic or basic activity, or strictly organic properties which are not compatible with autoanalyzer syringes, tubing, metal, and plastic parts. This reagent also contains surfactants that enhances the carrier-free matrix, decrease surface tension, promote effective mixing on a molecular level, and improve flow dynamics through tubing and syringes of automated analyzers. The concentration of reagent buffers, and other components, can be varied to compensate for limitations and variations in the configuration of sampling and reagent delivery systems of various makes of autoanalyzers. The reagent buffers also compensate for abnormal pH of urine samples and urines with high buffer capacities.

The reagent system for Leukocytes (WBC's) may consist of a single reagent, or a dual reagent system. The color generating mechanism of the reagent system is the same for the single or dual system, and is the result of Leukocyte esterase acting upon compatible esters. This ester/esterase reaction produces a relatively unstable indoxyl moiety that is oxidized to form an indigo color that is monitored by monochronatic spectrophotometry. To enhance the speed, completeness and specificity of the indoxyl moiety can be oxidized by the addition of a dehydrogenase to the reaction solution that will oxidize (replace) the alcohol group on the indoxyl group to yeild a ketone. This tranisitional indoxyl ketone radical formed will enhance color development specificity, accuracy, and sensitivity of the reaction. The reagent system may contain one or more of the following compounds, 2,4-dinotrophenylhydrazine, hydroxylamine, or semicarbizide, which in the presence of indoxide ketones will give color development that can be monitored at the same wavelength as the indigo. A further enhancement of the method concerning the indoxyl intermediate, is the addition of p-dimethylaminobenzaldehyde or p-Nitrobenzenediazonium tetrafluroborate (or other azo indicators), these will react with the intermediate to enhance color development at the afore mentioned wavelength. This reaction would enhance specificity, sensivitly, and accuracy. The reagent is buffered depending on which group or single component is used in the color developing reagent. The R2 if applicable also contains a buffer to adjust sample pH and to aid in solubility and compatibility of the R2's complex chemical matrix. This complex reagent matrix requires a complementary aqueous buffering system with unique dynamics capable of adjusting the reaction solution to the ideal pKa, and promoting component solution compatibility with autoanalyzers. Unbuffered solutions may have high acidic, or basic activity, or strictly organic properties which are not compatible with autoanalyzer syringes, tubing, metal, and plastic parts. This reagent system buffering is designed to correct these problems. The R2 (if applicable) also contains surfactants to decrease surface tension, promote effective mixing on a molecular level, aid in carrier-free matrix, and improve flow dynamics through tubing and syringes of automated analyzers. The preceding components and concentration of components of R1 and/or R2 reagents can be varied to compensate for limitations and variations in the configuration of sampling and reagent delivery systems of various makes of autoanalyzers. Without further elaboration, it is believed that one skilled in the art can, using the preceding description, effectively utilize the present invention. The following preferred specific embodiments are, therefore, to be construed as merely illustrative, and not limitive of the remainder of the disclosure of the present invention in any way whatsoever. In the following examples, all instrument parameters, reagent combinations, and method techniques are generalized.

EXAMPLE 1

The automated WBC urinalysis reagent system's single reagent system contains surfactant, 2,3-Butanedione monoxime, dimercaptopropanol, bile salts, albumin, calcium chloride, ethylenediametetraacetic acid, 3-indoyl acetate, and buffer. The reagent is then placed in the autoanalyzer.

The urine sample, standards, and controls are placed on the autoanalyzer specimen cups. The urine samples, standards, and controls are aliquoted into cuvettes, mixed with the reagent, and read at specified intervals as dictated by the instrument parameters at the specific wavelength (monochromatically) depending on reagent combination used. In this instance the assay should be read at 405 nanometers with read times specific to the analyzer.

EXAMPLE 2

The automated WBC urinalysis reagent system's first reagent (R1) contains surfactants, buffer, 2,3-Butanedione monoxime, ethylenediametetraacetic acid, dimercaptopropanol, bile salts, albumin, calcium chloride, and peroxidase. The second reagent (R2) consists of, some or all of the following: hydrogen peroxide, 3-indolyl acetate, N-toluene sulfonyl alanine indole ester, derivatized pyrrole amino acid ester, buffers, and/or surfactants. The reagents are placed on the autoanalyzer. The urine samples, standards, and controls are placed in the autoanalyzer specimen cups. The urine samples, standards, and controls, are aliquoted into cuvettes mixed with the first reagent, the second reagent is then added and mixed, and the solutions are then read at specified intervals as dictated by the instrument parameters at the specific wavelength (monochromatically) depending on the reagent combination used. In this instance the assay should be read at 405 nanometers with read time specific to the analyzer.

EXAMPLE 3

The automated WBC urinalysis reagent system's first reagent (R1) contains surfactants, buffer, bile salts, albumin, calcium chloride, 2,3- Butanedione monoxime, dimercaptopropanol, and ethylenediametetraacetic acid. The second reagent (R2) consists of some or all of the following: dehydrogenase, 3-indolyl acetate, N-toluene sulfonyl alanine indole ester, derivatized pyrrole amino acid ester, buffers, and/or surfactants. The reagents are placed on the autoanalyzer. The urine samples, standards, and controls are placed in the autoanalyzer specimen cups. The urine samples, standards, and controls, are aliquoted into cuvettes mixed with the first reagent, the second reagent is then added, and mixed, and the solutions are then read at specified intervals as dictated by the instrument parameters the specified wavelength (monochromatically) depending on the reagent combination used. In this instance the assay should be read at 405 nanometers, with read times specific to the analyzer.

EXAMPLE 4

The automated WBC urinalysis reagent system's first reagent (R1) contains sone or all of the following: surfactants, buffer, bile salts, albumin, calcium chloride, 2,3- Butanedione monoxime, ethylenediametetraacetic acid, dehydrogenase, 3-indolyl acetate, N-toluene sulfonyl alanine indole ester, and derivatized pyrrole amino acid ester. The second reagent (R2) consists of some or all of the following: 2,4-dinotrophenylhydrazine, 3- indolyl acetate, N-toluene sulfonyl alanine indole ester, derivatized pyrrole amino acid ester, buffers, and surfactants. The reagents are placed on the autoanalyzer. The urine samples, standards, and controls are placed in the autoanalyzer specimen cups. The urine samples, standards, and controls, are aliquoted into cuvettes, mixed with the first reagent, the second reagent is then added and mixed, and the solutions are then read at specified intervals as dictated by the instrument parameters at the specific wavelengths (monochromatically) depending on the reagent combination used. In this instance the assay should be read at 405 nanometers and read times specific to the analyzer.

EXAMPLE 5

The automated WBC urinalysis reagent system's first reagent (R1) contains some or all of the following: surfactants, buffer, bile salts, calcium chloride, albumin, 2,3-Butanedione monoxime, ethylenediametetraacetic acid, 3-indolyl acetate, N-toluene sulfonyl alanine indole ester, and/or derivatized pyrrole amino acid ester, are added. The second reagent (R2) consists of some or all of the following: p-dimethylaminobenzaldehyde, 3-indolyl acetate, N-toluene sulfonyl alanine indole ester, derivatized pyrrole amino acid ester, buffers, dilute hydrochloric acid, and surfactants. The reagents are placed on the autoanalyzer. The urine samples, standards, and controls are placed in the autoanalyzer specimen cups. The urine samples, standards, and controls, are aliquoted into cuvettes, mixed with the first reagent, the second reagent is then added and mixed, and the solutions are then read at specified intervals as dictated by the instrument parameters at the specified wavelength (monochromatically) depending on the reagent combination used. In this instance the assay should be read at 405 nanometers, with read times specific to the analyzer.

EXAMPLE 6

The automated WBC urinalysis reagent system's first reagent (R1) contains some or all of the following: surfactants, buffer, 2,3- Butanedione monoxime, ethylenediametetraacetic acid, bile salts, calcium chloride, and/or albumin. The second reagent (R2) consists of some, or all of the following: p-nitorphenyl stearate, phenyl laurate, buffers, and surfactants. The reagents are placed on the autoanalyzer. The urine samples, standards, and controls are placed in the autoanalyzer specimen cups. The urine samples, standards, and controls, are aliquoted into cuvettes, mixed with the first reagent, the second reagent is then added and mixed, and the solutions are then read at specified intervals as dictated by the instrument parameters at the specified wavelength (monochromatically) depending on the reagent combination used. In this instance, the assay should be read at 405 nanometers with read times specific to the analyzer.

The automated urinalysis system reagents are individually designed for optimum analysis of urinary components. The reagent system for pH of urine is carrier-independent, and has specific agents added to compensate for curve instability, and to improve accuracy, linearity, and precision. A buffer is added to enhance this reagent's linearity. The buffer's compositions, pH and pKa are dictated by the specific indicators included in the formulation. The concentrations of reagent buffers and other components can be varied to compensate for variations in the configuration of sampling and reagent delivery systems of different makes of autoanalyzers. The addition of buffers to compensate for urines with high buffer capacities that will cause interference with the pH assay is an obvious advancement over the previous art that had no primary buffer to stabilize color development and promote carrier-free-independence. The reagent also contains surfactants to enchance carrier-free matrix, decrease surface tension, promote effective mixing on a molecular level, and improve flow dynamics through tubing and syringes of automated analyzers.

The reagent system for pH can consist of two reagents, an R1 (reagent one of a two component system) and R2 (reagent two of a two component system), or just a single reagent, an R1. The color developing component of the reagent system is the water soluble indicators present in specific spectrophotometrically compatible groups in an aqueous solution that is compatible with autoanalyzers, components, and flow dynamics. These indicators may include, but are not limited to, Bromcresol green, Thymol Blue, Bromothymol Blue, Phenol red, Tropaeolin 000 no. 1, Alizarin yellow GG, Bromphenol red, and Chlorophenol red all of which can monitored spectrophotometrically. These indicators may be used singularly, or in any combination thereof, but only in the water-soluble salt form. The R2 if applicable, also contains a buffer to adjust sample pH and aid in solubility and compatibility of the reagent's complex chemical matrix. This complex chemical matrix requires a complimentary aqueous with unique dynamics capable of adjusting the reaction solution to the ideal pKa, and promoting reagent component solution compatibility with autoanalyzers. Unbuffered solutions may have high acidic or basic activity, or strictly organic properties which are not compatible with autoanalyzer syringes, tubing, metal, and plastic parts. The buffer also promotes carrier independence. The R2 (if applicable) also contains surfactants that allows enhance the carrier-free matrix, decrease surface tension, promote effective mixing on a molecular level, and improve flow dynamics through tubing and syringes of automated analyzers. The concentrations of components of the R1 and/or the R2 reagents can be varied to compensate for limitations and variations in the configuration of sampling and reagent delivery systems of various of makes of autoanalyzers. Without further elaboration, it is believed that one skilled in the art can, using the preceding description, effectively utilize the present invention to its fullest extent. The following preferred specific embodiments are meant to merely illustrate and not limit the remainder of the disclosure of this present invention in any way whatsoever. In the following examples, all automated instrument parameters, reagent combinations, and method techniques are generalized.

EXAMPLE 1

The automated pH urinalysis reagent system's single reagent system contains surfactant, buffers, Bromcresol green, Bromothymol blue, and Thymol Blue (note: these three indicators are balanced quantatively and compositionally to be in solution together to allow exact, and linear spectrophotometric extrapolation of results for pH). The reagent is placed on the autoanalyzer. The urine samples, standards, and controls are placed in the autoanalyzer specimen cups. The urine samples, standards, and controls, are aliquoted into cuvettes, mixed with the reagent, and read at specified intervals as dictated by the instrument parameters, and at the specified wavelength (monochromatically) depending on reagent combination used. In this instance the assay should be read at 600 nanometers, and read times are specific to the analyzer.

EXAMPLE 2

In the automated pH urinalysis single reagent system contains surfactants, buffer, Alizarin yellow, Tropaeolin 000 no. 1, Cresol red, Phenol Red, Bromphenol Red, Chlorophenol Red (note: these three indicators are balanced and designed to be in solution together to allow exact and linear spectrophotometric extrapolation of results for pH). The reagent is placed on the autoanalyzer. The urine samples, standards, and controls are placed in the autoanalyzer specimen cups. The urine sample, standards, and control, are aliquoted into cuvettes, mixed with the reagent, and read at specified intervals as dictated by the instrument parameters and at the specified wavelength (monochromatically) depending on reagent combination used. In this instance the assay should be read 405 nanometers and read times are specific to the analyzer.

The automated urinalysis system reagents are individually designed for their specific urinary component automated analysis in urine. The reagent system for Specific Gravity in urine is carrier independent, and has specific agents added to compensate for interference from, urinary protein, highly buffered urines, abnormal pH and other normal urinary constituents. The reagent system is composed of two reagents (but can consist of one reagent). The first reagent (R1) is specifically designed to neutralize matrix interference and increase sample-reagent compatibility with the autoanalyzer. A buffer is added to the first reagent (R1) to eliminate the affects of pH, highly buffered urines, and other interfering substances (which cause increase buffer affects) by nuetralizing pH. The buffer also aids in solubility and compatibility of the complex chemical matrix. This complex chemical reagent/sample matrix requires a complimentary buffering system with unique dynamics capable of adjusting reaction soultion to the ideal pKa, and promoting component solution compatibility with autoanalyzers. Unbuffered solutions may have high amount of acidic and basic activity, or strictly organic properties which are not compatible with autoanalyzer syringes, tubing, metal, plastic parts), and the buffer promotes carrier independence. The R1 also contains surfactants that enhance carrier free matrix, decrease surface tension, promote effective mixing on a molecular level, and improve flow dynamics through tubing and syringes of automated analyzers. Sodium Thiosulfate is added to the R1 to enhance color developement through the interaction which chloride present in urine (a major constituent). The R1 buffers constituents and concentrations can be varied in the to compensate for limitations and variations in the configuration of sampling and reagent delivery systems of various of makes of available autoanalyzers.

The reagent system for Specific Gravity second reagent (R2) is the color generating reagent of the 2 reagent set (unless a single reagent system for Specific Gravity is used). This second reagent R(2) is composed of methyl vinyl ether copolymers (which are sensitive to ions in solution). In the presence of ions in solution the vinyl group on the copolymer reacts with ions in solution via an exchange reaction that yields a hydrogen ion (H+). This exchange reactions effects a change in the pH of the solution which is measured by the color change of an indicator or combination of indictors including, but not limited to Thymol Blue, Bromothymol Blue, and Litmus. One or more of these indicators can be used in the R2. The advantage of using two or more indicators vs one would be broadening the range of the color development. Isopropyl alcohol is added to solubilize the copolymer. Please note that the prior art was restricted to a carrier solid phase method because the polymers could not solubilize to function independent of a carrier dependent solid matrix. The reagent is buffered to a specific pH depending on the active group linked to the vinyl copolymer and the corresponding indicators utilized for color development. The R2 also aids in solubility and compatibility of the reagents's complex chemical matrix. This complex chemical matrix requires a complimentary, aqueous buffering system with unique fluid dynamics capable of adjusting the reaction solution to the ideal pKa, promoting reagent solution compatibility with autoanalyzers. Unbuffered solutions may have acidic and basic activity, or strictly organic properties which are not compatible with autoanalyzer syringes, tubing, metal, and plastic parts, and promotes carrier independence. The R2 also contains surfactants that enhance carrier free matrix, decrease surface tension, promote effective mixing on a molecular level, and improve flow dynamics through tubing, and syringes of automated analyzers. The components and concentrations of components of R1 and/or the R2 reagents can be varied to compensate for limitations, and configuration of sampling and reagent delivery systems of various of makes of available autoanalyzers. Without further elaboration, it is believed that one skilled in the art can, using the preceding description, utilize the present invention to its fullest extent. The following preferred specific embodiments are, therefore, to be construed as merely illustrative, and not limit of the remainder of the disclosure in anyway whatsoever. In the following examples, all instrument parameters, reagent combinations, and method techniques are generalized.

EXAMPLE 1

In the automated urinalysis system reagents for Specific Gravity first reagent (R1), contains surfactant, Buffer, and Sodium Thiosulfate. The second reagent R2 consists of surfactant, buffer, methyl vinyl ether copolymer, BromoThymol Blue, and Isopropyl Alcohol. The reagents are placed on the autoanalyzer. The urine samples, standards, and controls are placed in the autoanalyzer specimen cups. The urine samples, standards, and controls, are aliquoted into cuvettes, mixed with the first reagent, the second reagent is then added and mixed, and the solution is read at specified intervals as dictated by the instrument parameters, and at the specified wavelength (monochromatically) depending on reagent combination used. In this instance, the assay should be read 660 nanometers, and read times are specific to the analyzer.

EXAMPLE 2

In the automated urinalysis system reagents for Specific Gravity first reagent (R1), contains surfactant, Buffer, and Sodium Thiosulfate. The second reagent R2 consists of surfactant, buffer, methyl vinyl ether copolymer, Bromothymol Blue, Thymol Blue and Isopropyl Alcohol. The reagents are placed on the autoanalyzer. The urine samples, standards, and controls are placed in the autoanalyzer specimen cups. The urine samples, standards, and controls, are aliquoted into cuvettes, mixed with the first reagent, the second reagent is then added and mixed, and the solution is read at specified intervals as dictated by the instrument parameters, and at the specified wavelength (monochromatically) depending on reagent combination used. In this instance, the assay should be read 600 nanometers, and read times are specific to the analyzer.

The automated urinalysis system reagents are individually designed for optimum analysis of specific urinary components automated analysis. The reagent system for Total Ketone Bodies in urine is carrier independent, and has specific agents added to compensate for interference from, enzyme inhibitors, highly pigmented urines, sulfhydryl groups, aytipcal color development, mesna (2-mercaptoethane sulfonic acid), levodopa, high ion levels (specific gravity), abnormal pH and other normal urinary constituents. The reagent system is composed of two reagents (but may consist of one system, one reagent). The first reagent (R1) is specifically designed to neutralize matrix interference and increase sample-reagent compatibility, with the autoanalyzer. The component 2,3-Butanedione monoxime is included in this first reagent (R1) to remove urea, and other substances found in urine that cause interference with the colormetric reaction. Ethylenediaminetetraacetic acid and dimercaptopropanol, are other components of the R1 that neutralize interfering substances by chelation, remove enzyme inhibitors, and anti-oxidant activity, These compounds removing oxidizing contaminants such as hypochlorite, and act as a solution clarifyer. It causes the disappearance of the characteristic yellow color of urine, thereby enhancing spectrophotometric analysis. Bile salts (exp:cholic acid sodium salt) are added to enhance solubility, enzyme activity, and prevent denaturation of the enzyme. Delta-3 hydroxybutyrate dehydrogenase is added to convert the B-hydroxybutyric acid (which composes 80% of Ketone Bodies present in urine) to acetoacetic acid. The prior art does not address this 80% fraction of the ketone bodies in urine. B-Nicotinamide Adenine Dinucleotide (NAD) is also included in the R1. The reaction of Delta-3 hydroxybutyrate dehydrogenase with the B-hydroxybutyric acid in the presence of NAD, results in the reduction of the NAD to B-Nicotinamide Adenine Dinucleotide (B-NADH). This reduction of NAD can be measured spectrophotometrically at 340 nm, and corresponds directly to the quantity of the B-Hydroxybutyric acid present. If desired the R1 as heretofore described, can stand as a single reagent for determination of Ketone Bodies. The total can be extrapolated from the B-Hydroxybutyric acid fraction by multiplying its concentration by 1.25 (to compensate for the 20% fraction of Total Ketone Bodies due to acetoacetic acid). The R1 also contains a buffer to adjust sample pH, establish carrier free matrix, aid in solubility, and compatibility of the reagents's complex chemical matrix. This complex chemical matrix requires a complementary aqueous buffering system with unique dynamics capable of adjusting the reaction solution to ideal pKa, and promoting reagent solution compatibility with autoanalyzers. Unbuffered solutions have high acidic, or basic activity, or strictly organic properties which are not compatible with autoanalyzer syringes, tubing, metal, and plastic parts. The buffer also promotes carrier independence. The R1 also contains surfactants that enhance the carrier free matrix, decrease surface tension, promote effective mixing on a molecular level, and improve flow dynamics through tubing, and syringes of automated analyzers. The concentrations R1 buffers, and other components can be varied to compensate for limitations, and variations in the configuration of sampling and reagent delivery systems of various makes of available autoanalyzers. The reagent buffers also compensate for abnormal pH of urine samples, and urines with high buffer capacities. The Total Ketone Bodies reagents system's second reagent (R2) is the color generating reagent of the 2 reagent set (unless a single reagent system is used). This second reagent is composed of Diazonium salts (e.g., 4-Nitrobenzene diazonium tetrafluroborate) which couples with the acetoacetic acid in the presence of sodium nitroferricyanide (or other alkaline metal dyes), yielding a hydrazo compound that can be monitored at 645 nm. Note, the R1 component, D-3-Hydroxybutyrate dehydrogenase converts B-Hydroxybutyric acid to acetoacetic acid. Thus, nearly all of the Ketone Bodies in urine (99%) are in the form of acetoacetic acid. The remaining 1% is acetone. As a result, this method measures 99% of ketones bodies compared to 20% measured by the prior art. The R2 also contains compounds to enhance sodium nitroferricyanide stability and the ensuing color development. These enhancers include (but are not limited to) alkali earth compounds metals,: phosphoric acid trimorpholide (in an alkaline buffer), ytrium (in an alkaline buffer), amine (or amine alcohols), and Ethylenediaminetetraacetic acid. The reagent is buffered according to which group, or single component is used in the color developing reaction. The R2 also contains a buffer to adjust sample pH and aid in solubility, and compatibility of the reagents complex chemical matrix. This complex chemical matrix requires a complementary, aqueous buffering system with unique dynamics capable of adjusting the reaction solution to the ideal pKa, and promoting reagent solution compatibility autoanalyzers. Unbuffered solutions may have high acidic and basic activity, or strictly organic properties which are not compatible with autoanalyzer use of syringes, tubing, metal, and plastic parts. The buffer also promotes carrier independence. The R2 also contains surfactants that enhance the carrier-free matrix, decrease surface tension, promote effective mixing on a molecular level, and improve flow dynamics through tubing and syringes of automated analyzers. The concentration and combination of components of the R1 and/or the R2 reagents can be varied to compensate for limitations, and variations in the configuration of sampling and reagent delivery systems of various makes of available autoanalyzers. Without further elaboration, it is believed that one skilled in the art can, using the preceding description, utilize the present invention to its fullest extent. The following preferred specific embodiments are, therefore, to be construed as merely illustrative, and not limit of the remainder of the disclosure in anyway whatsoever. In the following examples, all instrument parameters, reagent combinations, and method techniques are generalized.

EXAMPLE 1

The automated Total Ketone Bodies urinalysis reagent system's first reagent (R1) contains, surfactant, 2,3-Butanedione monoxime, ethylenediametetraacetic acid (sodium salt), dimercaptopropanol, bile salts, Delta-3-Hydroxybutyrate Dehydrogenase, NAD, and buffer. The second reagent R2 consist of surfactant, buffer, 4-Nitrobenzene diazonium tetrafluroborate, ethylenediametetraacetic acid (sodium salt), sodium nitroferricyanide, Ytrium, and phosphoric acid trimorpholide. The reagents are placed on the autoanalyzer. The urine samples, standards, and controls are placed in the autoanalyzer specimen cups. The urine samples, standards, and controls, are aliquoted into cuvettes, mixed with the first reagent, the second reagent is added and mixed, and the solution is read at specified intervals as dictated by the instrument parameters and at the specified wavelength (monochromatically) depending on reagent combination used. In this instance, the assay should be read 645 nanometers, and read times are specific to the analyzer.

EXAMPLE 2

The automated Total Ketone Bodies urinalysis reagent system's single reagent contains, 2,3-Butanedione monoxime, ethylenediametetraacetic acid, bile salts, dimercaptopropanol, NAD, B-3-Hydroxybutyrate Hydrogenase, buffers, and surfactants. The reagents are placed on the autoanalyzer. The urine samples, standards, and controls are placed in the autoanalyzer specimen cups. The urine samples, standards, and controls, are aliquoted into cuvettes, mixed with the reagent, and the solution is read at specified intervals as dictated by the instrument parameters and at the specified wavelength monochromatically depending on reagent combination used. In this instance the assay should be read at 340 nanometers wavelength and read times are specific to the analyzer.

EXAMPLE 3

In the automated Total Ketone Bodies urinalysis reagent system's first reagent (R1) contains surfactants, buffer, 2,3-Butanedione monoxime, ethylenediametetraacetic acid, are added. The second reagent (R2) consists of, buffer, 4-Nitrobenzene diazonium tetrafluroborate, ethylenediametetraacetic acid (sodium salt), sodium nitroferricyanide, Ytrium, and phosphoric acid trimorpholide. buffers, and surfactants. The reagents are placed on the autoanalyzer. The urine samples, standards, and controls are placed in the autoanalyzer specimen cups. The urine samples, standards, and controls, are aliquoted into cuvettes, mixed with the first reagent, the second reagent is added and mixed, and the solution is read at specified intervals as dictated by the instrument parameters, and at the specified wavelength (monochromatically) depending on reagent combination used. In this instance the assay should be read 645 nanometers and read times are is specific to the analyzer.

The automated urinalysis system reagents are individually designed for optimum analysis of their specific urinary components. The reagent system for Protein in urine is carrier independent and has specific agents added to compensate for interference from, highly pigmented urines, enzyme inhibitors, high ionic levels (specific gravity), abnormal pH (elevated), quaternary ammonium compounds (i.e., from some antiseptics, and detergents), or skin cleaners containing chlorhexidine, and other normal urinary constituents. The reagent system is composed of two reagents (but can consist of one reagent). The first reagent, (R1) is specifically designed to neutralize matrix interference and increase sample-reagent compatibility with the autoanalyzer. The compound 2,3-Butanedione monoxime is included in this first reagent (R1) to remove urea, and other substances found in urine that cause interference with the colormetric reaction. Ethylenediaminetetraacetic acid, and dimercaptopropanol, are other components of the R1 used to neutralize interfering substances by chelation, neutralization of enzyme inhibitors, and anti-oxidant activity, Thus by neutralizing contaminants such as hypochlorite. Also these components act as a solution clarifyers (when added to urine it causes the disappearance of the characteristic yellow color of urine, thus enhancing spectrophotometric analysis). Potassium chloride and sodium chloride are present to provide high ionic strength, which inturns increase solubilization of proteins. Succinate buffer and citrate buffer are present to optimize the pKa of the reagent system for analysis. The R1 also contains a buffer to aid in solubility and compatibility of multiple chemicals that require a mutual buffering system with unique dynamics, adjusting the reaction solution to the ideal pKa's, promotes reagent solution compatibility with autoanalyzers. Unbuffered solutions may have high acidic, or basic activity, or strictly organic properties which are not compatible with autoanalyzer syringes, tubing, metal, and plastic parts. The buffer also promotes carrier independence. The R1 also contains surfactants that enhance the carrier- free matrix, decrease surface tension, promote effective mixing on a molecular level, and improve flow dynamics through tubing and syringes of automated analyzers. The concentration of R1 buffers and other components can be varied to compensate for limitations and variations in the configuration of sampling and reagent delivery systems of various makes of autoanalyzers. The buffers also compensate for abnormal pH of urine and urines samples and urines with high buffer capacities.

The Protein reagent system's second reagent (R2) is the color generating reagent of the 2 reagent set (unless a single reagent system for Protein is used). This second reagent is composed of Copper sulfate in solution with sodium hydroxide, potassium iodide, sodium and/or potassium tartrate, and ARW-7 (wetting agent). The Cu++ ions bind with the unshared electrons in the nitrogen and oxygen atoms of proteins to form a blue-violet complex which can be measured spectrophotometrically at 540 nm. Bromcresol green exhibits a measurable dye-binding complex in the presence of albumin. Other indicators present are Coomassie Blue, tetrabromphenol blue, and 2,2'-biquinoline-4,4'-dicarboxylic acid disodium salt dihydrate (intensifies color development, thereby increasing sensitivity). The reagent is buffered depending on which group or single component is used in the color developing reaction. The R2 also contains a buffer to adjust sample pH, aid in solubility, and compatibility of these reagent's complex chemical matrix. This complex chemical matrix requires a complementary aqueous buffering system with unique dynamics capable of adjusting the reaction solution to the ideal pKa, and promoting reagent component solution compatibility with autoanalyzers. Unbuffered solutions may have high acidic, or basic activity, or strictly organic properties which are not compatible with autoanalyzer syringes, tubing, metal, and plastic parts. The buffering systems also promotes carrier independence. The R2 also contains surfactants that enhance the carrier-free matrix, decrease surface tension, promote effective mixing on a molecular level, and improve flow dynamics through tubing and syringes of automated analyzers. The concentrations and combinations of components of the R1 and/or the R2 reagents can be varied to compensate for limitations, and variations in the configuration of sampling and reagent delivery systems of various of makes of autoanalyzers. Without further elaboration, it is believed that one skilled in the art can, using the preceding description, effectively utilize the present invention. The following preferred specific embodiments are meant to merely illustrate, and not limit the remainder of the disclosure of the present invention in any way whatsoever. In the following examples, all instrument parameters, reagent combinations, and method techniques are generalized.

EXAMPLE 1

The automated Protein urinalysis reagents system's first reagent (R1) contains surfactant, 2,3-Butanedione monoxime, ethylenediametetraacetic acid (sodium salt), dimercaptopropanol, potassium chloride, sodium chloride, and buffer. The second reagent R2 consists of surfactant, buffer, copper sulfate, sodium hydroxide, potassium iodide, sodium and/or potassium tartrate, ARW-7, and 2,2'-biquinoline-4,4'-dicarboxylic acid disodium salt dihydrate. The reagents are placed on the autoanalyzer. The urine samples, standards, and controls are placed in the autoanalyzer specimen cups. The urine samples, standards, and controls are aliquoted into cuvettes, mixed with the first reagent, the second reagent is then added and mixed, and the solution is read at specified intervals as dictated by the instrument parameters at the specified wavelength (monochromatically) depending on the reagent combination used. In this instance the assay should be read 540 nanometers, with read times specific to the analyzer.

EXAMPLE 2

The automated Protein urinalysis reagent system's single reagent system contains 2,3-Butanedione monoxime, ethylenediametetraacetic acid, potassium chloride, sodium chloride, dimercaptopropanol, copper sulfate, sodium hydroxide, potassium iodide, sodium and/or potassium tartrate, 2,2'-biquinoline-4,4'-dicarboxylic acid disodium salt, buffers, and surfactants. The reagents are placed on the autoanalyzer. The urine samples, standards, and controls are placed in the autoanalyzer specimen cups. The urine samples, standards, and controls are aliquoted into cuvettes, mixed with the reagent, and the solution is read at specified intervals as dictated by the instrument parameters, and at the specified wavelength (monochromatically) depending on reagent combination used. In this instance the assay should be read at 540 nanometers wavelength, with read times specific to the analyzer.

EXAMPLE 3

The automated Protein urinalysis reagent system's first reagent (R1) contains surfactants, buffer, 2,3-Butanedione monoxime, ethylenediametetraacetic acid, dimercaptopropanol, succinate buffer, and bromcresol green. The reagents are placed on the autoanalyzer. The urine samples, standards, and controls are placed in the autoanalyzer specimen cups. The urine samples, standards, and controls are mixed with the first reagent, the second reagent then is aliquoted into cuvettes, added and mixed, and the solution is read at specified intervals as dictated by the instrument parameters, and at the specified wavelength bichromatically depending on reagent combination used. In this instance, the assay should be read at 660, and 750 nanometers, and read times are specific to the analyzer.

EXAMPLE 4

The automated Protein urinalysis reagent system's first reagent (R1) contains surfactant, 2,3-Butanedione monoxime, ethylenediametetraacetic acid (sodium salt), dimercaptopropanol, potassium chloride, sodium chloride, and buffer. The second reagent R2 consists of surfactant, succinate buffer, and bromcresol green. The reagents are placed on the autoanalyzer. The urine samples, standards, and controls are placed in the autoanalyzer specimen cups. The urine samples, standards, and controls are aliquoted into cuvettes, mixed with the first reagent, the second reagent is then added, and the solution is read at specified intervals as dictated by the instrument parameters, and at the specified wavelength (monochromatically) depending on reagent combination used. This assay should be read at 540 nanometers, and read times are is specific to the analyzer.

EXAMPLE 5

The automated Protein urinalysis reagent system's, first reagent (R1) contains surfactant, 2,3-Butanedione monoxime, ethylenediametetraacetic acid (sodium salt), dimercaptopropanol, potassium chloride, sodium chloride, and buffer. The second reagent, R2 consists of buffer, surfactant, and tetrabromphenol blue. The reagents are placed on the autoanalyzer. The urine samples, standards, and controls are placed in the autoanalyzer specimen cups. The urine samples, standards, and controls are aliquoted into cuvettes, mixed with the first reagent, the second reagent is then added and mixed, and the solution is read at specified intervals as dictated by the instrument parameters and at the specified wavelength (monochromatically) depending on reagent combination used. In this instance, the assay should be read at 600 nanometers, and read times are is specific to the analyzer.

EXAMPLE 6

The automated Protein urinalysis reagent system's the first reagent, (R1) contains surfactant, 2,3-Butanedione monoxime, ethylenediametetraacetic acid (sodium salt), dimercaptopropanol, potassium chloride, sodium chloride, and buffer. The second reagent, (R2) consists of buffer, surfactant, Coomassie blue, alcohol, and tetrabromphenol blue. The reagents are placed on the autoanalyzer. The urine samples, standards, and controls are placed in the autoanalyzer specimen cups. The urine samples, standards, and controls are aliquoted into cuvettes, mixed with the first reagent, the second reagent is then added and mixed, and the solution is read at specified intervals as dictated by the instrument parameters, and at the specific wavelength (monochromatically) depending on the reagent combination used. In this instance, the assay should be read at 600 nanometers, and read times are specific to the analyzer.

The automated Glucose urinalysis reagent system's are individually designed for optimum analysis of their specific urinary components. The reagent system for Glucose in urine is carrier independent, and has specific agents added to compensate for interference from enzyme inhibitors, Ketone Bodies, high ionic strength urine samples (specific gravity), Vitamin C, and other abnormal amounts urinary constituents. The reagent system is composed of two reagents (but can consist of one reagent). The first reagent (R1), is specifically designed to neutralize matrix interference and increase sample-reagent compatibility. The compound, 2,3-Butanedione monoxime, is included in this first reagent, (R1) to remove urea and other substances found in urine that cause interference with the colormetric reaction. Ethylenediaminetetraacetic acid and dimercaptopropanol are other components of the R1 that neutralize interfering substances by chelation, neutralize enzyme inhibitors, and anti-oxidant activity. These compounds remove oxidizing contaminants such as hypochlorite, and act as a solution clarifyers. They remove the characteristic yellow color of urine, thereby enhancing spectrophotometric analysis. This reagent may also contain Glucose oxidase which converts urinary glucose to gluconic acid. During oxidation, hydrogen peroxide is formed as a side product. Adenosine triphosphate (ATP) when added, in the presence of hexokinase will convert glucose to glucose-6-phosphate. Both of these compounds may be included in this reagent. The R1 also contains a buffer to adjust sample pH, and aid in solubility and compatibility of the reagent's complex chemical matrix. This complex matrix requires a complementary, aqueous buffering system with unique dynamics capable of adjusting the reaction solution to the ideal pKa and promoting the reagent component solution compatibility with autoanalyzers. Unbuffered solutions may have high of acidic or basic activity, or strictly organic properties which are not compatible with autoanalyzer syringes, tubing, metal, and plastic parts. The buffer also promotes carrier independence. The R1 also contains surfactants that enhance the carrier-free matrix, decrease surface tension, promote effective mixing on a molecular level, and improve flow dynamics through tubing and syringes of automated analyzers. The concentrations of R1 buffers and other components can be varied to compensate for limitations and variations in the configuration of sampling, and reagent delivery systems of various makes of autoanalyzers. The buffers also compensate for abnormal pH of urine samples and urines with high buffer capacities.

The Glucose reagent system's second reagent (R2), is the color generating reagent of the 2 reagent set (unless a single reagent system for Glucose is used). This second reagent is composed of one or more of the following: Peroxidase (which converts or oxidizes the newly formed hydrogen peroxide product of the glucose oxidase reaction, and releases an oxygen), o-Dianisidine, ampyrone, phenol, p-hydroxybenzoic acid, potassium iodide chromogen, and N-Ethyl-N-( 2-hydroxy-3-sulopropyl)-m-toluidine. The latter 7 can be used singularly, or in groups as couplers with Ampyrone (4-AA). The 4-AA is reduced by the oxygen released from the hydrogen peroxide/peroxidase reaction. Glucose-6-phosphate dehydrogenase is added to oxidize the glucose-6-phosphate present from the hexokinase reaction. NADP+ and/or NAD+ are added to acy as hydrogen acceptors from the glucose-6-phosphate, or the glucose dehydrogenase reaction. Note, glucose dehydrogenase is added to oxidize glucose to d-glucono-gamma-lactone. When this occurs NAD+ is reduced to NADH and can be monitored spectrophotometrically at 340 nm. The buffer is added to adjust sample pH, aid in solubility, and compatibility of the reagent complex chemical matrix. This complex chemical matrix requires a complementary, aqueous buffering system with unique dynamics capable of adjusting the reaction solution to the ideal pKa, and promoting the reagent component solution compatibility with autoanalyzers. Unbuffered solutions may have high acidic or basic activity, or strictly organic properties which are not compatible with autoanalyzer syringes, tubing, metal, and plastic parts. This buffer also promotes carrier independence. The R2 also contains surfactants that enhance the carrier-free matrix, decrease surface tension, promote effective mixing on a molecular level, and improve flow dynamics through tubing, and syringes of automated analyzers. The concentration and combination of components of the R1 and/or the R2 reagents can be varied to compensate for limitations, and variations in the configuration of sampling, and reagent delivery systems of various makes of autoanalyzers. Without further elaboration, it is believed that one skilled in the art can, using the preceding description, effectively utilize the present invention. The following preferred specific embodiments are meant to merely illustrate, and not limit the remainder of the disclosure of the present invention in any way whatsoever. In the following examples, all instrument parameters, reagent combinations, and method techniques are generalized.

EXAMPLE 1

The automated Glucose urinalysis reagent system's first reagent (R1), contains surfactant, 2,3-Butanedione monoxime, ethylenediametetraacetic acid (sodium salt), dimercaptopropanol, and buffer. The second reagent (R2), consists of surfactant, buffer, glucose oxidase, 4-AA, EHSPT (one or more of the following maybe substituted for: o-Dianisidine, ampyrone, phenol, p-hydroxybenzoic acid, potassium iodide chromogen, or N-Ethyl-N-(2-hydroxy-3-sulopropyl)-m-toluidine). The reagents are placed on the autoanalyzer. The urine samples, standards, and controls are placed in the autoanalyzer specimen cups. The urine samples, standards, and controls are aliquoted into cuvettes, mixed with the first reagent, the second reagent is then added and mixed, and the solution is read at specified intervals as dictated by the instrument parameters at the specified wavelength (monochromatically) depending on reagent combination used. In this instance the assay should be read at 555 nanometers, and read times are specific to the analyzer.

EXAMPLE 2

The automated Glucose urinalysis reagent system's first reagent (R1), contains 2,3-Butanedione monoxime, ethylenediaminetetraacetic acid, dimercaptopropanol, buffers, Glucose oxidase, and surfactants. The second reagent (R2), contains 4-AA, EHSPT (and one or more of the following: o-Dianisidine, ampyrone, phenol, p-hydroxybenzoic acid, potassium iodide chromogen, and N-Ethyl-N-(2-hydroxy-3-sulopropyl)-m-toluidine). The reagents are placed on the autoanalyzer. The urine samples, standards, and controls are placed in the autoanalyzer specimen cups. The urine samples, standards, and controls are aliquoted into cuvettes, mixed with the reagent's R1 and R2, and the solution is read at specified intervals as dictated by the instrument parameters at the specified wavelength (monochromatically) depending on reagent combination used. In this instance, the assay should be read at 555 nanometers and read times are specific to the analyzer.

EXAMPLE 3

The automated Glucose urinalysis reagent system's first reagent (R1), contains surfactants, buffer, 2,3-Butanedione monoxime, Glucose oxidase, ethylenediaminetetraacetic acid, dimercaptopropanol, and NAD+. In the second reagent (R2), contains glucose dehydrogenase, buffers, and surfactants. The reagents are placed on the autoanalyzer. The urine samples, standards, and controls are placed in the autoanalyzer specimen cups. The urine samples, standards, and controls are aliquoted into cuvettes, mixed with the first reagent, the second reagent is then added and mixed, and the solution is read at specified intervals as dictated by the instrument parameters and at the specified wavelength (monochromatically) depending on reagent combination used. In this instance the assay should be read at 340 nanometers, and read times are specific to the analyzer.

EXAMPLE 4

In the automated Glucose urinalysis reagent system's single reagent system (R1), contains surfactant, NAD+ or NADP+, 2,3-Butanedione monoxime, ethylenediametetraacetic acid, dimercaptopropanol, buffers, and Glucose oxidase. The reagents are placed on the autoanalyzer. The urine samples, standards, and controls are placed in the autoanalyzer specimen cups. The urine samples, standards, and controls are aliquoted into cuvettes, mixed with the reagent, and the solution is read at specified intervals as dictated by the instrument parameters, and at the specified wavelength (monochromatically) depending on reagent combination used. In this instance, the assay should be read at 340 nanometers, and read times are specific to the analyzer.

EXAMPLE 5

The automated Glucose urinalysis reagent system's first reagent (R1), contains surfactant, 2,3-Butanedione monoxime, ethylenediametetraacetic acid (sodium salt), dimercaptopropanol, and buffer. The second reagent R2, contains ATP, Hexokinase, Glucose-6-phosphate dehydrogenase, NADP+ and/or NAD+, buffer, and surfactant. The reagents are placed on the autoanalyzer. The urine samples, standards, and controls are placed in the autoanalyzer specimen cups. The urine samples, standards, and controls are aliquoted into cuvettes, mixed with the first reagent, the second reagent is then added and mixed, and the solution is read at specified intervals as dictated by the instrument parameters, and at the specified wavelength (monochromatically) depending on reagent combination used. In this instance, the assay should be read at 340 nanometers, and read times are specific to the analyzer.

EXAMPLE 6

The automated glucose urinalysis reagent system's first reagent (R1), contains surfactant, 2,3-Butanedione monoxime, ethylenediaminetetraacetic acid (sodium salt), dimercaptopropanol, ATP, Hexokinase, and buffer. The second reagent (R2), contains Glucose-6-phosphate dehydrogenase, NADP+ and/or NAD+, buffer, and surfactant. The reagents are placed in the autoanalyzer. The urine samples, standards, and controls are placed on the autoanalyzer specimen cups. The urine samples, standards, and controls are aliquoted into cuvettes, mixed with the first reagent, the second reagent is the added and mixed, and the solution is read at specified intervals as dictated by the instrument parameters, and at the specified wavelength (monochromatically) depending on reagent combination used. In this instance, the assay should be read at 340 nanometers, and read times are specific to the analyzer.

EXAMPLE 7

The automated Glucose urinalysis reagent system's first reagent (R1), contains surfactant, 2,3-Butanedione monoxime, ethylenediaminetetraacetic acid (sodium salt), dimercaptopropanol, and buffer. The second reagent R2, contains Glucose-6-phosphate dehydrogenase, NADP+ and/or NAD+, buffer, Glucose oxidase, Hexokinase, and surfactant. The reagents are placed on the autoanalyzer. The urine samples, standards, and controls are placed in the autoanalyzer specimen cups. The urine samples, standards, and controls are aliquoted into cuvettes, mixed with the first reagent, the second reagent is then added and mixed, and the solution is read at specified intervals as dictated by the instrument parameters, and at the specified wavelength (monochromatically) depending on reagent combination used. In this instance, the assay should be read at 340 nanometers, and read times are specific to the analyzer.

EXAMPLE 8

The automated Glucose urinalysis reagent system's single reagent (R1), system contains surfactant, 2,3-Butanedione monoxime, ethylenediametetraacetic acid (sodium salt), dimercaptopropanol, buffer, Glucose-6-phosphate dehydrogenase, NADP+ and/or NAD+, buffer, Glucose oxidase, and Hexokinase. The reagents are placed on the autoanalyzer. The urine samples, standards, and controls are placed in the autoanalyzer specimen cups. The urine samples, standards, and controls are aliquoted into cuvettes, mixed with the first reagent, the second reagent is the added and mixed, and the solution is read at specified intervals as dictated by the instrument parameters, and at the specified wavelength (monochromatically) depending on reagent combination used. In this instance, the assay should be read at 340 nanometers, and read times are specific to the analyzer.

The automated urinalysis system reagents are individually designed for optimum analysis of specific urinary components. The reagent system for Bacterial Reductase/Nitrite/Indole activity (as a measure for bacterial uremia) in urine is carrier independent, and has specific agents added to compensate for interference from enzyme inhibitors, and other abnormal amounts of urinary constituents. The reagent system is composed of two reagents, but can be consist of one reagent. The first reagent (R1), is specifically designed to neutralize matrix interference, and increase sample to liquid reagent compatibility with the autoanalyzer. The component, 2,3-Butanedione monoxime, is included in this first reagent (R1) to remove urea, and other substances found in urine that cause interference with the colormetric reaction. Ethylenediaminetetraacetic acid, and dimercaptopropanol are other components of the R1 that neutralize interfering substances by chelation, inactivation of enzyme inhibitors, and anti-oxidant activity. These compounds remove oxidizing contaminants such as hypochlorite, and act as solution clarifyers (i.e., they absorb or cause the disappearance of the characteristic yellow color of urine), thereby enhancing spectrophotometric analysis. Oxidized Glutathione (GSSG) in one of several analytical pathways is present to act as a substrate for the bacterial reductase. B-Nicotinamide Adenine Dinucleotide Phosphate (reduced form, NADPH), and/or Nicotinamide Adenine Dinucleotide (reduced form, NADH) are present to act as coenzymes for the reductase enzyme reaction. Utilizing another analytical pathway the R1 would would contain the above referenced components to neutralize sample matrix interference and one or more of the following: Sulfuric acid, Phosphoric acid, p-Arsanilic acid, Sulfanilamide, N-Sulfanilylsulfanilamide, and/or sodium iodide (or other salt forms). The R1 also contains a buffer to adjust sample pH, aid in solubility and compatibility of the reagent's complex chemical matrix. This complex chemical matrix requires a complementary aqueous buffering system with unique dynamics capable of adjusting reaction solution to the ideal pKa and promoting reagent component solution compatibility with autoanalyzers. Unbuffered solutions may have high acidic or basic activity, or strictly organic properties which are not compatible with autoanalyzer syringes, tubing, metal, and plastic parts. The buffer also promotes carrier independence. The R1 also contains surfactants that enhance the carrier free matrix, decrease surface tension, promote effective mixing on a molecular level, and improve flow dynamics through tubing and syringes of automated analyzers. The R1 buffers constituents and concentrations can be varied to compensate for variations in the configuration of sampling, and reagent delivery systems of various makes of autoanalyzers. The buffers also compensate for abnormal pH of urine and urines with high buffering capacities.

The Bacterial Reductase/Nitrite/Indole reagent system's second reagent (R2) is the color generating reagent of the 2 reagent set unless a single reagent system is used. This second reagent (R2) may utilize a reaction pathway that requires one or more of the following: GSSG, NADPH, and NADH. p-Dimethy-aminobenzaldehyde (DMABA) is an indicator for aerobic and anaerobic activity correlated to indole production. Utilizing another analytical pathway the R2 would contain one or more of the following: a salt of iodide (Na, K, etc. . . . ), N-(1-napthyl)ethylenediamine, 1,2,3,4,-Tetrahydroisoquinoline hydrochloric acid, 4-Nitrobenzenediazonium tetrafluroborate, or another suitable azo dye that forms a complex with the diazonium salt, which can be measured spectrophotometrically at 540 nm. This second reagent (R2) may utilize a reaction pathway that requires one or more of the following: Triphenyltetrazolium chloride act as a substrate for the bacterial reductase, and when reduced yields a colormetrically measurable compound. In the presence of the NADH and/or NADPH reduced triphenyltetrazolium chloride will also yield a color reaction at 340 nanometers. The buffers are added to adjust sample pH, aid in solubility, and compatibility of the reagent's complex chemical matrix. This complex chemical matrix requires a complementary aqueous buffering system with unique dynamics capable of adjusting the reaction solution to the ideal pKa, and promoting reagent component solution compatibility with autoanalyzers. Unbuffered solutions may have high acidic and basic activity, or strictly organic properties which are not compatible with autoanalyzer syringes, tubing, metal, and plastic parts. The buffers also promote carrier independence. The R2 also contains surfactants that enhance the carrier free matrix, decrease surface tension, promote effective mixing on a molecular level, and improve flow dynamics through tubing and syringes of automated analyzers. The preceding components and the concentrations of the components of the R1 and/or the R2 reagents can be varied to compensate for limitations, variations in the configuration of sampling, and reagent delivery systems of various of makes of autoanalyzers. The above constituents can be varied, to compensate for said differences. Without further elaboration, it is believed that one skilled in the art can, using the preceding description, can effectively utilize the present invention. The following preferred specific embodiments are, therefore, to be construed as merely illustrative, and not limitive of the remainder of the disclosure in anyway whatsoever. In the following examples, all instrument parameters, reagent combinations, and method techniques are generalized.

EXAMPLE 1

In the automated urinalysis system reagents for Bacterial reductase assay in the first reagent (R1), contains surfactant, 2,3-Butanedione monoxime, ethylenediaminetetraacetic acid (sodium salt), dimercaptopropanol, buffer. The second reagent R2 consist of surfactant, buffer, GSSH, NADPH and or NADH. The reagents are placed in the autoanalyzer. The urine sample, standards, and controls are placed in the autoanalyzer specimen cups. The urine sample, standards, and control, are mixed with the first reagent, then the second reagent is added, and the solution is mixed, and read at specified intervals as dictated by the instrument parameters, and at the specified wavelength (monochromatically) depending on reagent combination used. In this instance the assay should be read 340 nanometers and read times are specific to the analyzer.

EXAMPLE 2

In the automated urinalysis system reagent for Bacterial reductase in the dual reagent system, 2,3-Butanedione monoxime, ethylenediaminetetraacetic acid, dimercaptopropanol, buffers, sulfanilamide, phosphoric acid (or another suitable acid), surfactants, are added. In the R2 N-(1-naphthyl)ethylenediamine and or 1,2,3,4,-Tetrahydroisoquinoline hydrochloric acid, or 1,2,3,4-tetrahydrobenzoquinolin- 3-ol (or other suitable azo dye), The reagents are placed in the autoanalyzer. The urine sample, standards, and controls are placed in the autoanalyzer specimen cups. The urine sample, standards, and control, are mixed with the reagent, and the solution is read at specified intervals as dictated by the instrument parameters and at the specified wavelength monochromatically depending on reagent combination used. In this instance the assay should be read at 540 nanometers wavelength and read times are specific to the analyzer.

EXAMPLE 3

In the automated urinalysis system reagents for Bacterial reductase, the first reagent (R1), contains surfactants, buffer, 2,3-Butanedione monoxime, Glucose oxidase, ethylenediaminetetraacetic acid, and dimercaptopropanol. In the R2 (second reagent) p-arsanilic acid, 1,2,3,4-tetrahydrobenzoquinolin-3-ol, buffers, and surfactants are added. The reagents are placed in the autoanalyzer. The urine samples, standards, and controls are placed in the autoanalyzer specimen cups. The urine samples, standards, and controls, are mixed with the first reagent, then the second reagent is added, and the solution is mixed, read at specified intervals as dictated by the instrument parameters, and at the specified wavelength monochromatically depending on reagent combination used. In this instance the assay should be read 540 nanometers and read times are specific to the analyzer.

EXAMPLE 4

In the automated urinalysis system reagents for Bacterial reductase in the single reagent system (R1), contains surfactant, NADH and or NADPH, 2,3-Butanedione monoxime, ethylenediaminetetraacetic acid, dimercaptopropanol, buffers, GSSH. The reagents are placed in the autoanalyzer. The urine samples, standards, and controls are placed in the autoanalyzer specimen cups. The urine samples, standards, and controls, are mixed with the first reagent, then the second reagent is added, and the solution is mixed, and read at specified intervals as dictated by the instrument parameters at the specified wavelength (monochromatically) depending on reagent combination used. In this instance the assay should be read 340 nanometers and read times are specific to the analyzer.

EXAMPLE 5

In the automated urinalysis system reagents for Bacterial reductase, the first reagent (R1), contains surfactant, 2,3-Butanedione monoxime, ethylenediaminetetraacetic acid (sodium salt), dimercaptopropanol, sulfuric acid, and buffer. The second reagent R2 consist of potassium iodide, starch, buffer, and surfactant. The reagents are placed in the autoanalyzer. The urine samples, standards, and controls are placed in the autoanalyzer specimen cups. The urine samples, standards, and control, are mixed with the first reagent, then the second reagent is added, and the solution is mixed, and read at specified intervals as dictated by the instrument parameters, and at the specified wavelength (monochromatically) depending on reagent combination used. In this instance the assay should be read 600 nanometers and read times are specific to the analyzer.

EXAMPLE 6

In the automated urinalysis system reagents for Bacterial reductase first reagent (R1), contains surfactant, 2,3-Butanedione monoxime, ethylenediaminetetraacetic acid (sodium salt), dimercaptopropanol, and buffer. The second reagent R2 consist of Triphenyltetrazolium chloride, NADPH and or NADH, buffer, and surfactant. The reagents are placed on the autoanalyzer. The urine samples, standards, and controls are placed in the autoanalyzer specimen cups. The urine samples, standards, and controls are mixed with the first reagent, then the second reagent is added, and the solution is mixed, and read at specified intervals as dictated by the instrument parameters, and at the specified wavelength (monochromatically) depending on reagent combination used. In this instance the assay should be read 340 nanometers and read times are is specific to the analyzer.

EXAMPLE 7

In the automated urinalysis system reagents for Bacterial reductase assay in the first reagent (R1), contains surfactant, 2,3-Butanedione monoxime, ethylenediaminetetraacec acid (sodium salt), dimercaptopropanol, buffer. The second reagent R2 consist of surfactant, buffer, p-Dimethylaminobenzaldehyde (DMABA). The reagents are placed in the autoanalyzer. The urine sample, standards, and controls are placed in the autoanalyzer specimen cups. The urine samples, standards, and control are mixed with the first reagent, then the second reagent is added, and the solution is mixed, and read at specified intervals as dictated by the instrument parameters, and at the specified wavelength (monochromatically) depending on reagent combination used. In this instance the assay should be read 540 nanometers and read times are specific to the analyzer.

From the foregoing it is believed that those familiar with the art will readily recognize and appreciate the novel concepts and features of the present invention. Numerous variations, changes and substitutions of equivalents will present themselves from persons skilled in the art and may be made without necessarily departing from the scope and principles of this invention. Therefore the invention has been described with reference to a number of its embodiment, it can nevertheless be arbitrarily varied within the scope of the following claims.

What is claimed is:

1. A method for detecting white blood cells in a patient's urine comprising placing an aliquot of the urine to be tested in an automated analyzer sampling cup, placing the cup in a sampling tray within the automated analyzer, transferring the urine to a cuvette mounted within the automated analyzer, injecting at least one reagent composition in an aqueous medium into the cuvette, the reagent composition containing a buffer to adjust the pH of the urine to a preferred value, a surfactant, at least two compounds to remove substances in the urine that cause interference with colorimetric photometry selected from the group consisting of 2,3-butanedione monoxime, ethylenediaminetetraacetic acid, dimercaptopropanol, bile salts, albumin, calcium chloride, peroxidase, hydrogen peroxide, dehydrogenase, 3-indolzol acetate, N-toluene sulfonyl alanine indole ester and pyrrole amino acid ester, together with a color indicator to quantitatively determine white blood cells in the urine, reading at specified intervals, in accordance with a preprogrammed code introduced into the automated analyzer, at a preprogrammed monochromatically specified wavelength, to compare absorbance of the patient's urine and reagent composition complex with that of a standard containing a known concentration of white blood cells and thereby determining the presence or absence of white blood cells in the patient's urine.

2. The method according to claim 1 wherein there is a first and second reagent composition in an aqueous medium injected into the cuvette.

3. The method according to claim 1 wherein the wavelength of the analyzer is about 405 nanometers.

4. The method according to claim 1 wherein said at least one reagent composition further comprises a first reagent composition comprising a buffer to adjust the pH of the urine to a preferred value, a surfactant, 2,3-butanedione and a compound to remove substances in the urine that cause interference with colorimetric photometry further selected from the group consisting of bile salts, albumin, calcium chloride, dimercaptopropanol and ethylenediaminetetraacetic acid, and a second reagent composition comprising a buffer, a surfactant, a color indicator and a compound selected from the group consisting of dehydrogenase, 3-indolzol acetate, N-toluene sulfonyl alanine indole ester, and pyrrole amino acid ester.

* * * * *